United States Patent [19]

Collins et al.

[11] Patent Number: 5,847,120

[45] Date of Patent: Dec. 8, 1998

[54] LONG-LIVED HOMOGENOUS OXIDATION CATALYSTS

[75] Inventors: Terrence J. Collins; Scott W. Gordon-Wylie, both of Pittsburgh, Pa.

[73] Assignee: Carnegie Mellon University, Pittsburgh, Pa.

[21] Appl. No.: 681,237

[22] Filed: Jul. 22, 1996

[51] Int. Cl.$^6$ .................................................. C07D 257/02

[52] U.S. Cl. ...................... 540/460; 540/480; 540/482; 540/483

[58] Field of Search ..................................... 540/460, 480, 540/482, 483

[56] References Cited

U.S. PATENT DOCUMENTS

| | | |
|---|---|---|
| 4,577,042 | 3/1986 | Collins et al. ........................... 564/158 |
| 4,758,682 | 7/1996 | Collins et al. ........................... 556/137 |

OTHER PUBLICATIONS

Polyhedron, 14, 9, pp. 1117–1127, Shakir et al. "A New Synthetic Route For the Preparation of a New Series of 14–22 Membered Tetraoxomacrocyclic Tetramines and Their Transition Metal Complexes".

A. Paul Krapcho, Edwin G. E. Jahngen, Jr., and David S. Kashdan, Route to Monoesters of Malonic Acids, Tetrahedron Letters Nos. 32, pp. 2721–2723, 1994.

G. A. Fletcher and J. H. Jones, A List of Amino–Acid Derivatives Which Are Useful in Peptide Synthesis, Int. J. Peptide Protein Res. 4, 1972, 347–371, Jun. 10, 1972.

Jose M. Workman, Routes to Multimetallic High Oxidation State Transition Metal Complexes, Metal Complexes, Carnegie Mellon University, Mellon College of Science, Jul. 23, 1992.

Terrence J. Collins, Designing Ligands for Oxidizing Complexes, Department of Chemistry, Carnegie Mellon University, Accounts of Chemical Research, 1994, 27, p. 279.

Masaru Nakamura, Mitsuko Toda and Hiroko Saito, Fluorimetric Determination of Aromatuc Aldehydes With 4,5–Dimethoxyl–1,2–Diaminobenzene, Analytica Chimica Acta, 134 (1982) 39–45.

Erich Stuart Uffelman, Macrocyclic Tetraamido–N Ligands that Stabilize High Valent Complexes of Chromium, Maganese, Iron, Cobalt, Nickel and Copper, California Institute of Technology, Aug. 19, 1991.

Theodora W. Greene, Protective Groups in Organic Synthesis, Harvard University, John Wiley & Sons, 1981.

Kimberly K. Kostka, Synthesis and Characterization of High–Valent Iron Complexes of Macrocyclic Tetraamido–N Ligands, Carnegie Mellon University, jul. 19, 1993.

Nathan L. Drake, Harry D. Anspon, et al. Synthetic Antimarlarials. Some Derivativs of 8–Aminoquinoline, Laboratories of the University of Maryland, vol. 68, p. 1536, Aug. 1946.

Richard J. Bushby and Michael D. Pollard, The Introduction of Alkylidene Substituents into the 4–position of the 3,3,5, 5,–Tetramethyl–$\Delta$–pyrazoline Nucleus by the Thioketone plus Diazoalkane Reaction: Synthesis of Tetrasubstituted Episulphides and Alkenes.

Primary Examiner—Yogendra N. Gupta
Attorney, Agent, or Firm—Kirkpatrick & Lockhart LLP

[57] ABSTRACT

A robust chelate complex is provided having the formula:

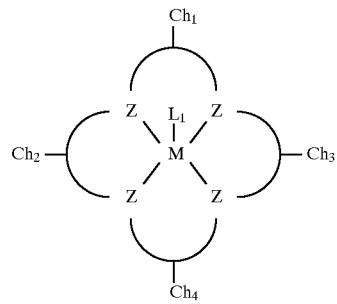

wherein

M is a metal, preferably a transition metal; Z is an anionic donor atom, at least three of which are nitrogen and the other is preferably nitrogen or oxygen; $L_1$ is a labile ligand;

$Ch_1$, $Ch_2$ and $Ch_3$ are oxidation resistant chelate groups which are the same or different and which form 5 or 6 membered rings with the metal, and $Ch_4$ is a chelate group having the structure

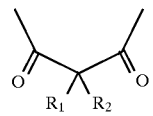

wherein $R_1$ and $R_2$ are the same or different and are preferably selected from the group consisting of hydrogen, halogen, methyl, and $CF_3$ or when linked, a five or six membered ring cyclo substituent. The complex provides a stable, long-lived oxidation catalyst or catalyst activator.

4 Claims, 4 Drawing Sheets

LONG-LIVED HOMOGENOUS OXIDATION CATALYSTS

This work was supported by the National Institutes of Health, GM-44867 and the National Science Foundation CHE9319505. The U.S. government may have rights in this invention.

BACKGROUND OF THE INVENTION

1. Field of the Invention

This invention relates to metal chelate complexes for forming oxidation catalysts, and more particularly, to long-lived macrocyclic oxidation catalysts capable of catalyzing demanding oxidations with peroxidic and related primary oxidants.

2. Description of the Invention Background

While transition metal-based systems provide the major source of oxidants in both chemistry and biology, oxidation chemistry is much better developed in the latter area, i.e., many difficult selective oxidation reactions that are accomplished in biological processes have not been achieved in homogeneous synthetic systems. This difference is more glaring for oxidation chemistry than for any other major branch of reaction chemistry. Thus, compared with reduction chemistry or carbon-carbon bond forming chemistry, oxidation chemistry is still severely limited in the number and quality of the available technologies for stoichiometric or catalytic processes.

The relative dearth of good homogeneous oxidation systems and catalysts is believed to be due to oxidative degradation. Complexes of high oxidation state middle and later transition metal ions, analogous to those that function as active intermediates in numerous enzymatic oxidations, have been difficult to attain synthetically because of the tendency of such complexes to quickly degrade their ligands.

In Collins, T. J., "Designing Ligands for Oxidizing Complexes," *Accounts of Chemical Research*, 279, Vol. 27, No. 9 (1994), synthetic metal-based oxidants are conceptually separated into two classes, metalloredox-active oxidants and metallotemplate oxidants. In metalloredox-active systems, the oxidizing moiety contains the metal ion which is in direct contact with the ligands. Consequently, these systems are limited by the small supply of ligands that are compatible with oxidizing metal ions. Metallotemplate oxidants are not limited in such a way because the oxidizing entity is more remote from the metal ion, but metallotemplate systems are useful only for mild as opposed to rigorous oxidations that require highly reactive metalloxidants. The metal ion oxidants in oxygenase enzymes often catalyze rigorous oxidations such as the methane monooxygenase reaction, i.e., the oxidation of methane to methanol with oxygen as the primary oxidant. The roles of the metallo-oxidants in such enzymes are of the metalloredox-active type. Thus, a key to moving this spectacular enzymatic chemistry into man-made systems lies in conquering the challenge of developing robust ligand systems that can tolerate extremely strongly oxidizing metal ions of the atom-abstractor type.

In the *Accounts* article, Collins describes a design-oriented approach to formation of ligands and metal chelate complexes that are resistant to oxidative degradation. The *Accounts* article highlights a set of rules for attaining ligand systems that are inert to oxidative degradation. Several diamido-N-diphenoxido acyclic and tetraamido-N macrocyclic ligands, developed to be resistant to oxidative degradation, are also illustrated in the *Accounts* article, as are middle and later transition metal complexes where the metal ions are in rare or unprecedented high oxidation states attainable by employing the macrocyclic ligands.

While being sufficient to allow preparation of the described rare high valent ions in stable form, including strong electrotransfer oxidants, the set of rules of the *Accounts* article is incomplete for achieving the goal of encapsulating an especially powerful metal-oxo oxidant similar to those found in monooxygenase enzymes such that the oxidant has a sufficient lifetime to carry out bi-molecular oxidations. Attainment of such a goal had to wait to the developments in ligand design described herein.

SUMMARY OF THE INVENTION

The desired ligand and derivative complex stabilities are met by the macrocylic tetradentate ligand compound of the present invention. The compounds have the general formula,

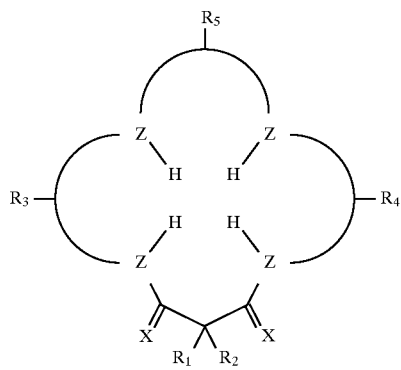

wherein $R_1$ and $R_2$ are the same or different, linked or nonlinked, and are selected from substituents that are unreactive, form strong bonds with the cyclic carbon, are sterically hindered, are conformationally hindered and combinations thereof sufficient for restricting the substituent from intramolecular oxidative degradation.

The hindrance prevents attainment of conformers that are conducive to intramolecular oxidative degradation.

Z is an oxidation resistant metal-complexing atom, such as N or O, bearing hydrogen where necessary;

X is an oxidation resistant functionality such as O or an $NR_s$ wherein $R_s$ is methyl, phenyl, hydroxyl, oxylic, —$CF_3$ or —$CH_2CF_3$;

$R_3$ is a unit joining the adjacent Z atoms comprised of

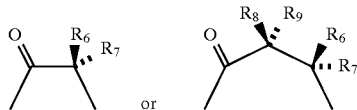

$R_4$ is a unit joining the adjacent Z atoms comprised of

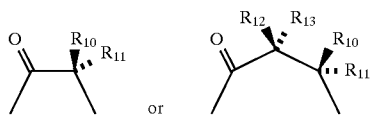

wherein $R_6$ and $R_7$, $R_8$ and $R_9$, and $R_{10}$ and $R_{11}$, and $R_{12}$ and $R_{13}$, pairwise and cumulatively, are the same or different and are selected from the group consisting of alkyl, aryl, hydrogen, halogens, $CF_3$ and combinations thereof; and $R_5$ is a unit joining the adjacent Z atoms comprised of:

(i)

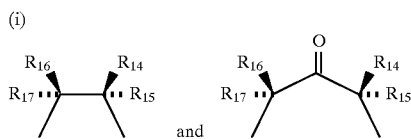

and wherein $R_{14}$ through $R_{17}$ are the same or different and are alkyl, aryl, hydrogen, halogen, $CF_3$ or combinations thereof, and (ii) an aryl group including

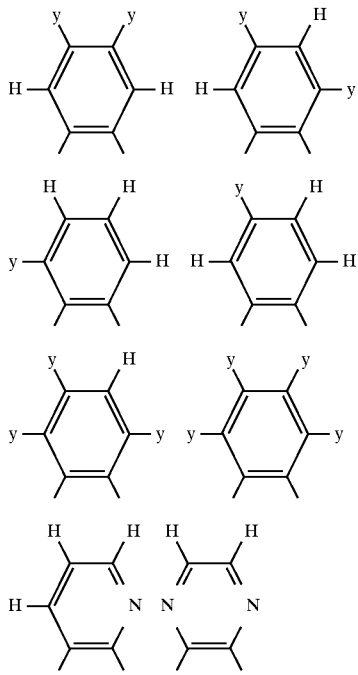

wherein Y is any substituent or substituents, but preferably halogen, hydrogen, alkyl, aryl, amino, substituted amino, nitro, alkoxy, aryloxy and combinations thereof. The aryl group formulation replaces the four substituents, and the carbon atoms to which they are attached.

The present invention pertains to the novel changes to the macrocyclic structure that increase the robustness of tetra-aza macrocyclic ligands such that one can obtain ligand systems that can support catalysis based on purported highly reactive metal-oxo intermediates similar to those of the monoxygenases. The degradation chemistry that required the described changes was completely unexpected. Most significantly, the new systems described herein support catalysis with highly desirable O-atom transfer oxidants, especially peroxides, making them available for a wide range of technological oxidation applications where there is significant promise of obtaining chemically- and cost-effective catalyses.

Transition metal complexes of macrocyclic ligands have been used to catalyze oxidations in the past. Patented systems include porphyrins and phthalocyanines, halogenated porphyrins and ligands related to porphyrins, and substituted tricycloazanonane and related macrocycles. All of these systems differ fundamentally from the system of the present invention in significant ways. First, the macrocylic tetraamides are tetraanionic and highly donating such that the ligands of the present invention render accessible the reactive high valent states of metals much better than any of the other macrocycles employed. Second, the macrocycles of the present invention can attain a high degree of protection with or without recourse to halogen substituents—the nonhalogenated species have a higher degree of environmental friendliness. Third, complexes of the macrocyclic tetraamides of the present invention exhibit a pronounced resistance to hydrolysis making them suitable for use in-protic media, such as water, in which various metal ion salts are soluble.

The tetradentate macrocyclic compound of the present invention is designed to be complexed with a metal, preferably a transition metal, and most preferably a group VIA (Cr group), VIIA (Mn group), VIII (Fe, Co, Ni groups) and IB (Cu group) transition metal, (now referred to as groups 6, 7, 8, 9, 10 and 11 of the Periodic Table of the Elements using the new nomenclature) to form the corresponding chelate complex.

The invention therefore also includes a chelate complex of the formula

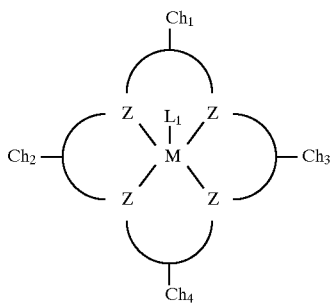

wherein M is a metal, Z is the oxidation resistant metal complexing atom described in the macrocyclic tetradentate compound of the invention above, $L_1$ is any labile ligand, and $Ch_1$, $Ch_2$, $Ch_3$ and $Ch_4$ are oxidation resistant components of the chelate system which are the same or different and which form five- to six-membered rings with the adjacent ZMZ atoms.

In the preferred embodiment, the axial ligand, $L_1$, is labile because it occupies its position relative to the metal until the chelate system is introduced into a solution containing an oxidant. The labile ligand will dissociate in solution and will be replaced by the oxidant, most generally an O-atom transfer agent, but also any general oxidant that can serve to activate the metal ion to perform catalysis. Preferred labile ligands include the Cl-anion, halide ions in general, $CN^-$, ROH, NH3, or any amine, carboxylate, phenol or phenoxide, nitrile, pyridine, ether, sulfoxide, ketone, or carbonate.

It has been determined that the oxidation site in iron complexes of aromatic ring-containing macrocycles (one electron oxidized above the $Fe^{III}$ state) can be manipulated by choice of the axial ligands as well as by the aromatic ring substituents. Strong σ-donor anionic axial ligands ($CN^-$) favor a metal-centered oxidation i.e., $Fe^{IV}$, whereas weaker donors (e.g., $Cl^-$) favor a ligand-localized oxidation. The oxo intermediate form of the chelate complex system is believed to function as the actual catalyst in some applications. In others, the chelate system can be the sole site of oxidation, or the oxidation site can be mixed between the chelate system, the metal and any other ligand attached to the metal.

The chelate group $Ch_1$ is preferably the constituent described above as $R_5$ of the macrocyclic tetradentate compound. $Ch_2$ and $Ch_3$ correspond to the units $R_3$ and $R_4$, respectively, of the macrocyclic tetradentate compound described above.

$Ch_4$ is preferably a linking constituent having the general formula $X='CC(R'')_2'C=X$ wherein $(R'')_2$ is equivalent to $R_1$ and $R_2$ described above and X is the oxidation resistant functionality described above.

$R_1$ and $R_2$ are key substituents in the design of the robust chelate complex and catalysts of the present invention. $R_1$ and $R_2$ are preferably methyl, $CF_3$, hydrogen or halogen, or may form, together with the carbon atom to which both are bound, a five-membered ring. It is believed that intramolecular reactions between the $R_1$ and $R_2$ substituents in prior art complexes and an oxo ligand in a functioning catalytic system contribute to the rapid degradation of the chelate ligand as has been heretofore experienced. See FIG. 1 for a proposed mechanism of oxidative degradation of the catalyst. It has been observed, for example, consistent with FIG. 1, that known catalyst compounds having diethyl substituents in the $R_1$, $R_2$ positions are sensitive to oxidative attack such that, while catalytic oxidations can be observed, the ligand system simultaneously undergoes slow oxidative degradation. All of the tetraamide macrocycles described in the Collins, *Accounts of Chemical Research* article cited above include the diethyl substituents in the $R_1$, $R_2$ positions. Thus, no macrocyclic tetraamide ligand transition metal complex has been shown heretofore to be competent to carry out useful oxidation catalyses by virtue of a significant longevity of the catalyst system.

DETAILED DESCRIPTION OF THE PREFERRED EMBODIMENTS

Figure 1:
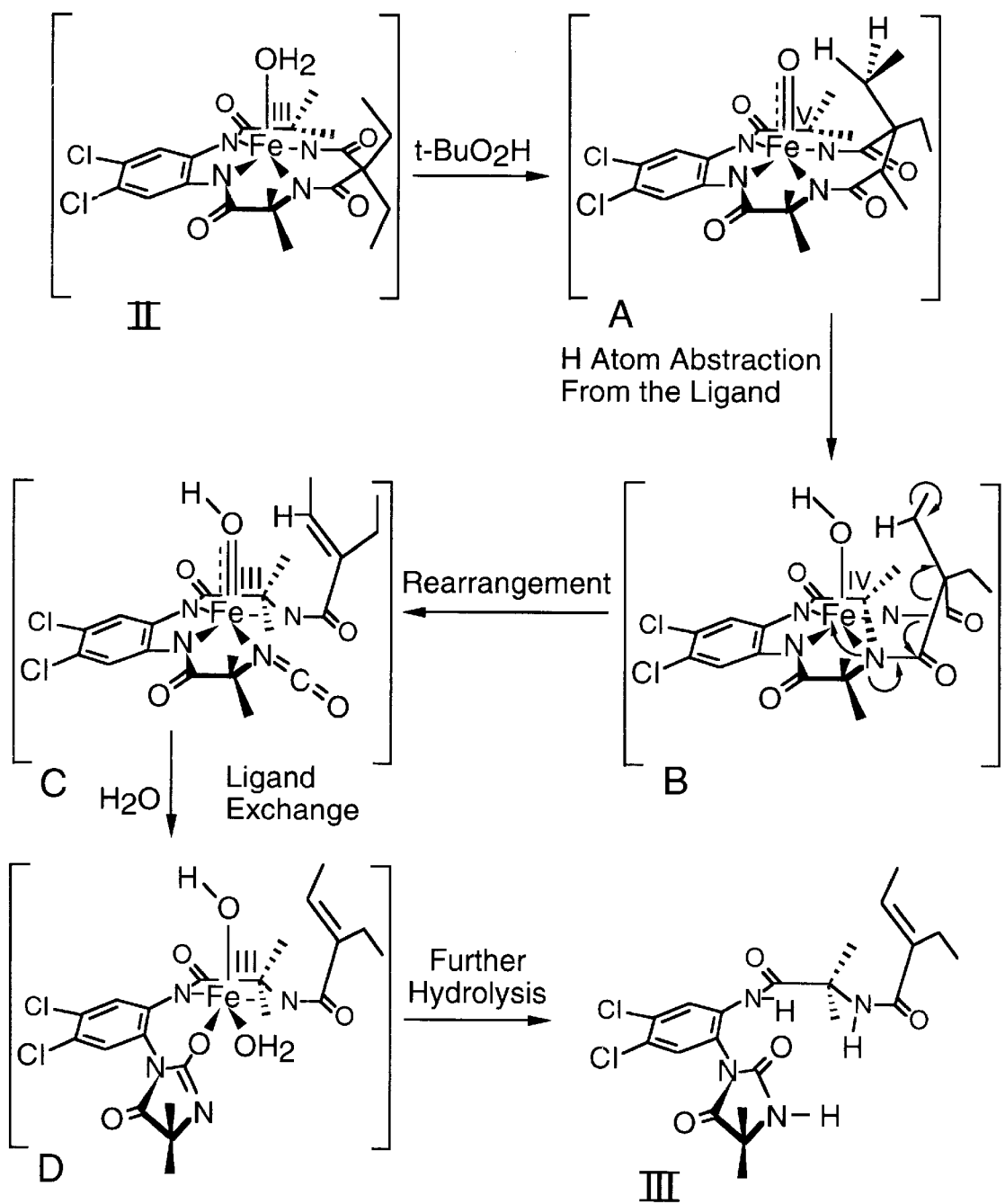
FIG. 1 is a schematic illustration of the proposed path of oxidative ligand degradation of a catalyst system consisting of compound II and peroxides due to intramolecular reactions between a diethyl substituent and the oxo axial ligand.

The preferred embodiment of the tetradentate macrocyclic compound of the present invention follows:

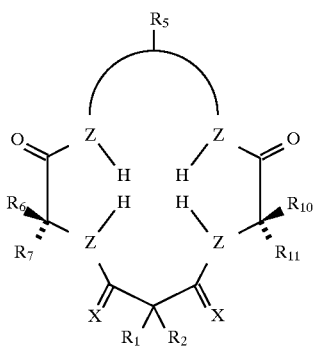

wherein:

$R_1$ and $R_2$ are the same or different and are selected from the group of substituents that are unreactive, form strong bonds with the cyclic carbon, are sterically hindered, are conformationally hindered and combinations thereof sufficient for restricting the substituent from intramolecular oxidative degradation. The low conformational freedom of the species prevents attainment of conformers that are conducive to intramolecular oxidative degradation. Z is an oxidation resistant metal complexing atom, preferably N or O, bearing H where necessary. Preferably at least three Z's are N. X is an oxidation resistant functionality, preferably O or $NR_s$ wherein $R_s$ is methyl, phenyl, hydroxyl, oxylic, $-CF_3$ or $-CH_2CF_3$.

$R_6$, $R_7$, $R_{10}$ and $R_{11}$ are the same or different and are selected from the group consisting of alkyl, aryl, hydrogen, halogens and $CF_3$. $R_5$ is a unit joining the adjacent Z atoms and is selected from the group consisting of: (i)

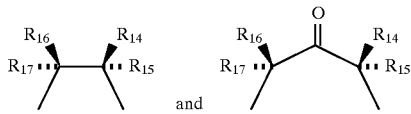

wherein $R_{14}$ through $R_{17}$ are the same or different and alkyl, aryl, hydrogen, halogen, $CF_3$ or combinations thereof, and (ii) an aryl group including

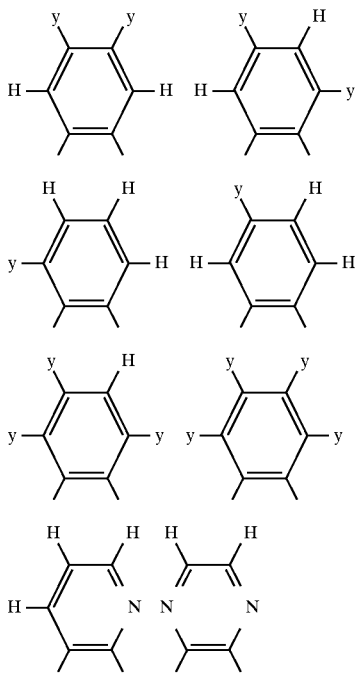

wherein Y is halogen, hydrogen, alkyl, aryl, amino, substituted amino, nitro, alkoxy, aryloxy and combinations thereof.

The compounds of the present invention form robust, long-lived oxidation catalysts and precatalysts. For the sake of convenience, and without limiting the scope of the invention, "catalyst" will be used herein to include precatalysts and actual catalyst complexes, where the latter is the species that carries out the oxidation. In many cases, the precise catalytic mechanism is not known and thus the precise role in any given oxidation reaction of the chelate system of the present invention may not be known. As used herein, robust oxidation catalyst means that when the catalyst is added to a solvent in the presence of an oxidant, such as a peroxide, the half-life of the activated form of the metal complex is 30 seconds or more. The half-life is the time in which half of the metal complex decomposes or degrades.

Surprisingly, the design of one of the most preferred embodiments of the new robust compounds differs from the prior art compounds by only one constituent. By changing the $R_1$, $R_2$ diethyl substituents of the prior art tetraamido compounds to dimethyl substituents, the previously fragile, short-lived chelate complexes are transformed unexpectedly into stable, long-lived complexes which are very resistant to oxidative degradation. What appeared to be a minor change in the structure is in fact the key to a new class of robust long-lived oxidation catalysts. The C-H bond strength of the methyl substituent is about 3 Kcal.mol$^{-1}$ greater than the C-H bond strength of the corresponding ethyl substituent. It has been determined that any $R_1$, $R_2$ substituents which are unreactive, or which form strong bonds with the cyclic carbon, or are sterically or conformational hindered, such that they are restricted from intramolecular reaction with the axial oxo ligand will also form the robust catalysts, or precatalysts of the invention.

The importance of the bond strength and/or conformational constraints can be seen from the following determinations.

In order to support oxidation catalysis, every component of the ligand system must be substantially resistant to oxidative degradation. The key to the stability of the $R_1$ and $R_2$ groups has been determined by observation in a particularly informative case. As shown in FIG. 1, iron (III) aqua complexes react with hydroperoxides to give a purported oxo complex which it has been shown exhibit catalytic properties for the oxidation of nitriles containing C-H bounds α to the cyano group. However, as catalysis proceeds the ligand system slowly decomposes and it is proposed that this degradation proceeds via abstraction of an H-atom from a methylene group of an ethyl substituent in the $R_1$ position as is consistent with the structure of the hydantoin-ring containing degradation product, labeled III (FIG. 1). Molecular models reveal that a highly strained conformation of the $Ch_4$—containing chelate ring is required to bring the abstractable H-atom close to the abstracting O-atom. Compound III has been unambiguously characterized by a variety of mass spectrometric, $^1H$ and $^{13}C$ NMR, IR, elemental analyses. Simultaneously with the observed degradation, the system catalytically oxidizes the weakest C-H bond in a series of nitrites [$(CH_3)_2CHCN$, $CH_3CH2CN$, $CH_3CN$, $CD_3CN$] which are employed as solvents. The products are mixtures of nitrile oxidation products. Thus, where t-butyl hydroperoxide is the primary oxidant, the product mixture with $(CH_3)_2CHCN$ as the substrate contains $(CH_3)_2C(OH)CN$, $(CH_3)_2(CN)COOC(CH_3)_3$, $(CH_3)_2(CN)COOCH_3$, $(CH_3)_2C=O$, $(CH_3)_3COH$. It has also been shown that while this product mixture suggests a free radical autoxidation process where the role of the iron complex, II (FIG. 1), would be to initiate the process, free radical autoxidation cannot be the dominant mechanism. Thus, when the oxidation is carried out under $^{18}O_2$ (1 atm, >98%) the yield of $^{18}O_2$ labelled products is too low for the reaction mechanism to be consistent with a completely free radical autoxidation process. By replacement of $CH_3$— for $CH_3CH_2$— in the $R_1$ and $R_2$ positions, the ligand degradation is dramatically suppressed such that nitrile oxidation alone dominates the oxidative reactivity. This inhibition of ligand degradation by the $CH_3$— for $CH_3CH_2$— can be rationalized as resulting from the increased C-H bond strength of $CH_3$— versus $CH_3C_2$—, ca.$^3$ kcal/mol$^{-1}$, thereby slowing the rate of the H-atom abstraction by the oxo ligand by ca. three orders of magnitude. Since it is apparent that the abstraction is critical to the degradation, the orientation of the abstractable H-atom with respect to the oxo ligand is also critical as this orientation determines the distance of approach and abstraction reactions are exquisitely distance dependent. Molecular models reveal that if a cyclopentyl unit is employed to replace the ethyl groups of $R_1$ and $R_2$, the methylenic C-H group equivalent to that abstracted from the ethyl C-H group cannot reach the oxo ligand without considerably more ring-strain than that found in the ethyl case. Thus, the conformational constraint approach serves to dramatically increase the resistance of a so-substituted chelate to oxidative degradation.

Figure 2:
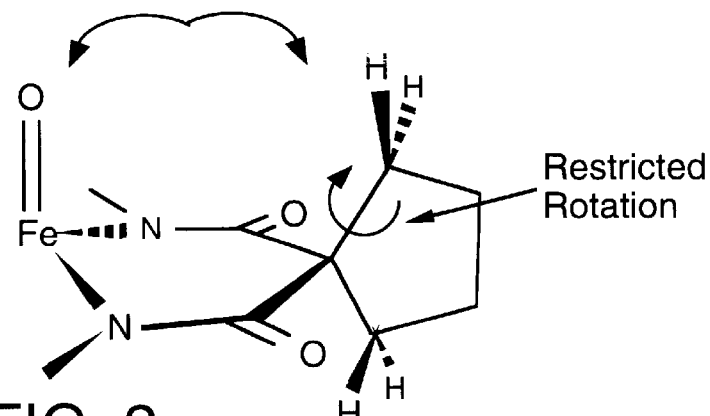
FIG. 2 is an illustration of the manner in which conformational constraints prevent oxidative degradation of the oxo group.

In the structure shown in FIG. 2, the oxo group and methylenic H are restricted from as close an approach as in the ethyl case because the methylene group of the cyclopentyl substituent cannot rotate freely to bring the two groups into as close a juxaposition.

The compounds of the present invention are macrocyclic, comprised of four anionic donor ligands which result in concert to form a substantially planar tetradentate platform which can be complexed with a metal and axial ligand to form the chelate/catalyst system of the present invention. The preferred design for producing robust ligands is a macrocyclic tetraamido ligand having no hydrogens α to N-amido donor groups. When coordinated with the metal ion, five- and six-membered chelate rings are most stable. The substituents can vary considerably provided they meet the requirements described above. This is particularly critical for the $R_1$ and $R_2$ substituents.

An azide based synthetic route to macrocyclic tetraamido ligands is described in Uffelman, E. S., Ph.D. Thesis, California Institute of Technology, (1992). Alternatively, and preferably, the compounds of the present invention can be synthesized by a new synthetic route, described in co-pending U.S. patent application of S. W. Gordon-Wylie et al., "Synthesis of Macrocyclic Tetraamido-N Ligands", filed on even date herewith, the disclosure of which is incorporated herein by reference.

Figure 3A:
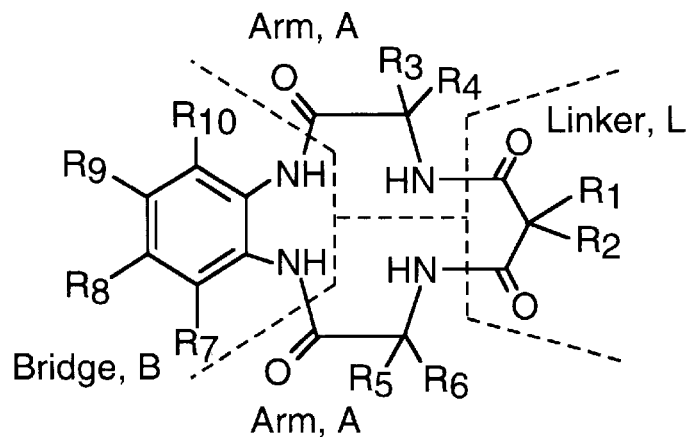
FIGS. 3(a) and (b) are illustrations of two possible structures of the macrocyclic tetraamide ligand of the present invention showing the arm, linker and bridge components of the compound.
Figure 3B:
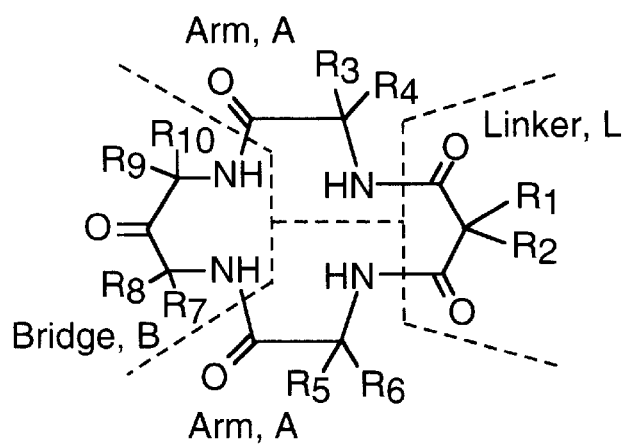

The new synthesis method permits the synthesis of variants which cannot be synthesized via the prior art azide based method. In varying the macrocycle, however, it is important to preserve the general framework of the compound. The macrocycle will be made up of 5- and 6-membered rings, in a 5,5,5,6 pattern, a 5,6,5,6 pattern, a 5,6,6,6 pattern, or a 6,6,6,6 ring pattern discussed in more detail below The new synthetic method proceeds generally as shown in sequences 1 and 2 below. Specific examples of the application of the new method to the synthesis of some particular macrocyclic tetraamides are shown in sequence 3. For convenience of classification herein, the starting materials that are composed of diamine functionalities are sometimes referred to as "Bridges" (B), the starting materials composed of diacid functionalities are sometimes referred to as "Linkers" (L), and the starting materials composed of amine/acid functionalities are sometimes referred to as "Arms" (A). See FIGS. 3(a) and (b). The arms of the macrocyclic compound are far more robust than the linker and are resistant to degradative attacks.

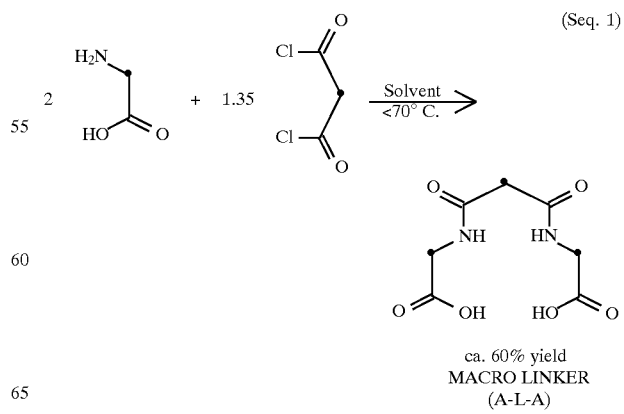

(Seq. 1)

ca. 60% yield
MACRO LINKER
(A-L-A)

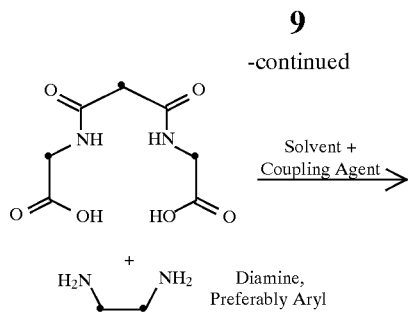

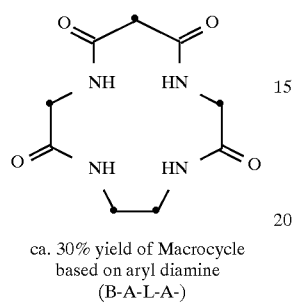

ca. 30% yield of Macrocycle based on aryl diamine (B-A-L-A-)

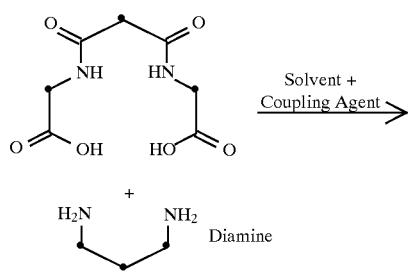

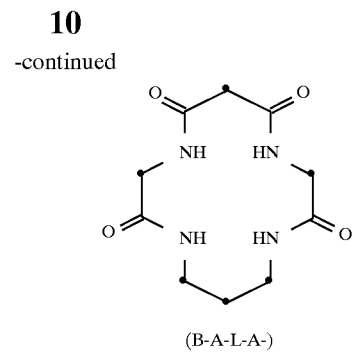

(B-A-L-A-)

Sequence 1 is a generalized synthesis of macrocyclic tetraamides having a (B-A-L-A-) configuration, from α-amino carboxylic acids via the new synthetic method. A diamide dicarboxyl-containing intermediate, sometimes referred to herein by the short hand designation, "macro linker intermediate" or simply the "intermediate" (A-L-A) is preformed without the use of protecting groups via a selective double coupling reaction wherein an a amino carboxylic acid, the arms, A, and an activated malonic acid derivative, the linker, L, in solvent are heated to form the macro linker intermediate. The macro linker intermediate is then coupled to a diamine, the bridge, B, in another selective double coupling reaction that employs a solvent, a coupling agent and heat. The synthetic methodology is highly streamlined and tolerates a wide range of functional groups. A wide range of macrocyclic tetraamides bearing different electronic or steric substituents have been prepared in this manner in good yield.

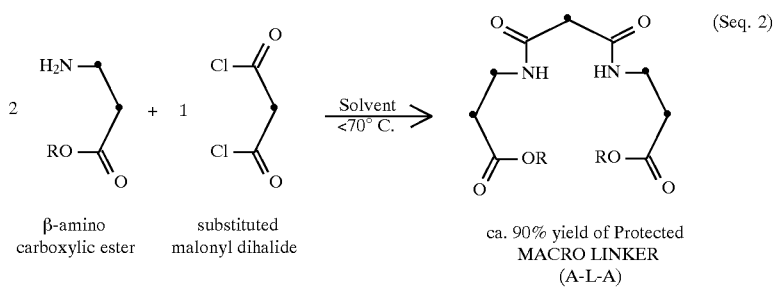

(Seq. 2)

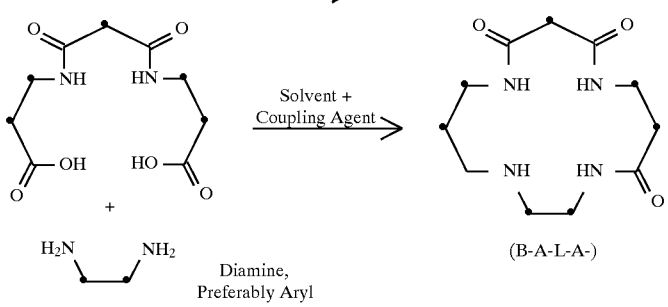

-continued

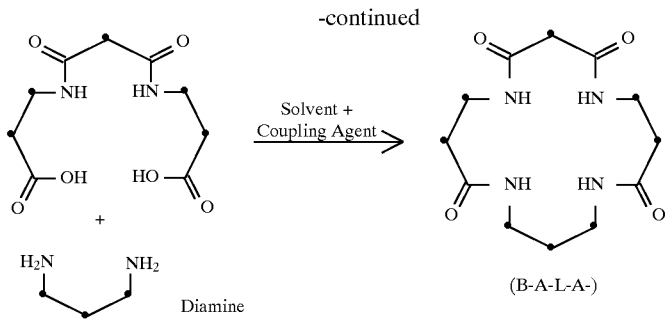

Sequence 2 is a generalized synthesis of macrocyclic tetraamides having a (B-A-L-A-) configuration, from β-amino carboxylic acids via a modified version of the basic, or primary, synthetic method. The basic same approach employed with α-amino carboxylic acid starting materials is applied to β-amino carboxylic acid starting materials. For some β-amino carboxylic acids, use of a protecting group may be desirable, as shown in Sequence 2. A macro linker intermediate (A-L-A) is preformed via a selective double coupling reaction wherein a protected β-amino carboxylic ester arm, A, and an activated malonic acid derivative linker, L, in solvent are heated to form the intermediate, which, after deprotection can then be coupled to the diamine bridge, B, in another selective double coupling reaction to yield a wide variety of substituted macrocyclic tetraamides with an expanded ring size compared to those that have been prepared from α-amino carboxylic acids.

The macro linker intermediate (A-L-A) can be made on a large scale in batch or continuous processing via direct reaction of a substituted malonyl dihalide with a solution (preferably a pyridine solution) of an α or β-amino carboxylic acid or ester. Many examples of the reaction proceed in good yield without protecting groups at temperatures preferably less than or equal to about 70° C. Some examples may require the use of protecting groups and these reactions generally proceed in good yield. The intermediate can be separated into batches and each separate batch further reacted with a wide range of diamine bridging compounds having different steric or electronic substituents in the presence of a coupling agent. For the α-amino carboxylic acid case, the ring closing step proceeds for 48–120 hours and is ideally substantially moisture free. See Sequence 3. A wide range of tetraamido macrocycles having finely tuned electronic properties can be synthesized at a considerable cost savings over the prior art azide method.

Seq. (3)

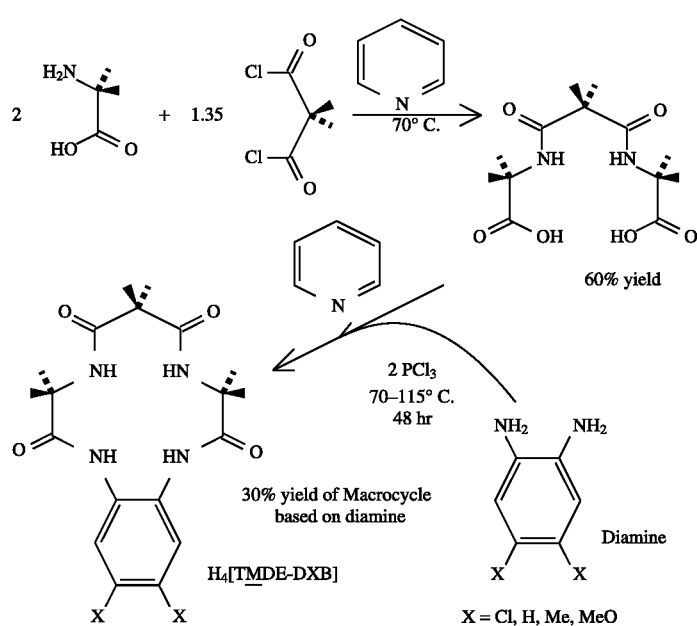

Sequence 3 is a specific example of the preparation of a macrocyclic tetraamide having a (B-A-L-A-) configuration from α-amino carboxylic acid starting materials. An α-amino carboxylic acid is mixed with an activated malonate in pyridine at temperatures less than 70° C. After the selective double coupling reaction is complete, 72–144 hrs, the macro linker intermediate (A-L-A) is isolated. In a second step a diamine, preferably an o-phenylene diamine, is added to a pyridine solution of the macro linker intermediate in the presence of a coupling agent, preferably $PCl_3$ or pivaloyl chloride. The ring closure, a double coupling reaction, is allowed to proceed at reflux for 48–110 hrs, and then the desired macrocyclic tetraamide is isolated in good yield.

The synthesis of oxidatively robust macrocyclic tetraamides requires that all H atoms α to the donor atoms be replaced by more oxidatively robust groups such as alkyl, halo, aryl or heterocyclic substituents.

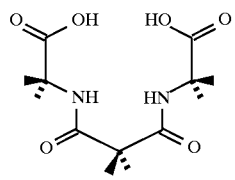

Structure 1

Structure 1 shows the key intermediate in the production of the catalyst of the present invention, an oxidatively robust macro linker (Arm-Linker-Arm). This molecule can be readily synthesized in one step without the use of protecting groups via the direct acylation of α-methylalanine with dimethyl malonyl dichloride.

In an alternative embodiment, the method of the invention uses protection/deprotection sequences to generate a protected form of the macro linker intermediate. Upon deprotection, the intermediate is coupled via the double coupling reaction described above to generate the tetraamido macrocycle. Similarly, protection/deprotection sequences can be applied to substituents present on the bridging unit to expand the range of bridging substituents that can be utilized in the macrocyclization reaction.

Both embodiments of the method of the invention rely heavily on the amine and carboxylic acid based starting materials hereinafter listed in Table 1. Table 1 lists several forms of the starting materials in what is designated the parent, protected/activated and hidden forms of the amine and carboxylic acid functionalities in a general sense. Table 2 utilizes these categories in conjunction with chelation ring size constraints (5- and 6-membered chelate rings are preferred) in order to identify useful starting materials for the synthesis of chelating macrocyclic tetraamide compounds having the desired five- or six-membered ring.

As used herein "parent groups" (shown in italics in Table 1) define a preferred synthetic functionality. "Protected/activated groups" refers to those groups that contain an easily recognizable portion of the parent group. "Hidden groups" as used herein refers to those groups that need not contain an easily recognizable portion of the parent group but which are capable of ready conversion to the parent group or to a protected/activated form of the parent group. More detailed examples may readily be found in Greene and Greene, "Protective Groups in Organic Synthesis", John Wiley and Sons, New York (1981). An extensive list of protecting/activating groups particularly suitable for peptide synthesis may be found in G. A. Fletcher and J. H. Jones, "A List of Amino-Acid Derivatives Which are Useful in Peptide Synthesis", Int. J. Peptide Protein Res. 4, (1972), p.347–371.

TABLE 1

| Protected/<br>Activated<br>Amines<br>Acids | Hidden<br>Amines | Protected/<br>Activated<br>Carboxylic Acids | Hidden<br>Carboxylic |
|---|---|---|---|
| N-alkyl<br>amines | azides | activated esters | nitriles |

TABLE 1-continued

| Protected/<br>Activated<br>Amines<br>Acids | Hidden<br>Amines | Protected/<br>Activated<br>Carboxylic Acids | Hidden<br>Carboxylic |
|---|---|---|---|
| amides | azo compounds | acyl halides | oxazolines |
| amino acetals | imides | amides | |
| N-benzyls | isocyanates | anhydrides | |
| carbamates | isothiocyanates | hydrazides | |
| enamines | nitrilium ions | O-acyl oximes | |
| hydrazines | nitro compounds | oxazolidines | |
| imines | phosphazos | oxazalones | |
| N-oxides | | phosphite esters | |
| N-phosphinyls | | silyl esters | |
| N-phosphoryls | | stannyl esters | |
| N-Metal derivatives | | substituted benzyl esters | |
| silyl amines (N—Si) | | substituted ethyl esters | |
| N-Sulfenyls | | substituted methyl esters | |
| sulfonamides | | sulfonyl esters | |
| N-Sulfonyls | | sulfenyl esters | |
| urea derivatives | | | |

Structure 2 is used herein to define the shorthand notation shown in Table 2 and Table 3 that specifies the chelate ring sizes (including the metal ion) that are formed when a given macrocyclic ligand is coordinated to a transition metal center.

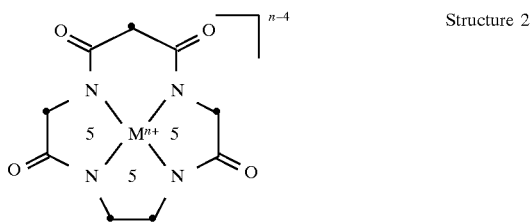

Structure 2

Amine is designated by "a", and carboxylate by "c". Dashes (-) indicate amide bonds. Every dash must connect a trailing "a" to a leading "c" or vice versa, the final dash wraps around to the beginning. Structure 2 illustrates a (5,5,6,5) macrocyclic ligand shown in metal coordinated form with chelate ring sizes (including the metal ion) indicated. Using a counterclockwise rotation, the specific macrocycle employed is 5aa-5ca-6cc-5ac- (or any cyclic permutation thereof).

The parent (=) forms of the functional groups for each starting material are shown pictorially in Table 2 below, while possible combinations of protected/activated (p/a) or hidden (h) forms for each starting material are shown in tabular form. Variable positions are marked with a bullet (●). The underlined side captions are in a shorthand notation that refers to chelation ring sizes formed when the particular starting material is incorporated into a macrocycle and coordinated to a metal center. (See Structure 2)

TABLE 2
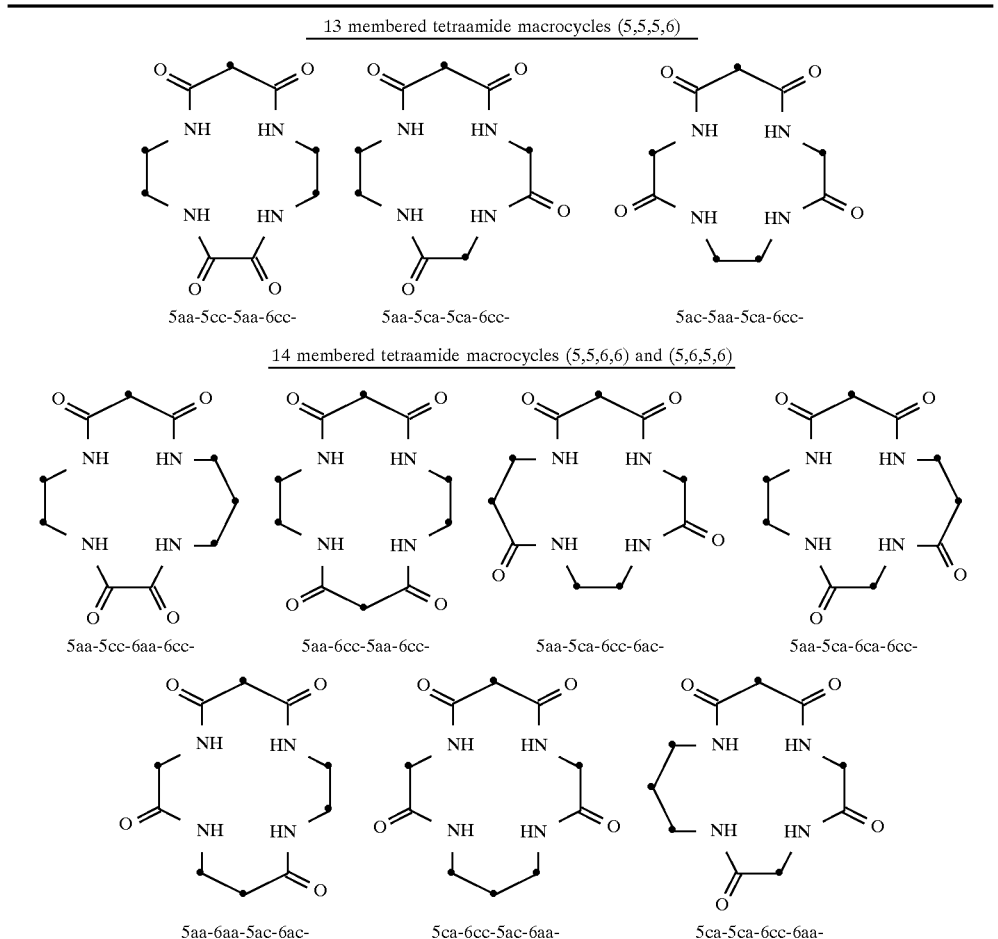
The complete range of macrocyclic tetraamide compounds able to be synthesized from the starting materials identified in Table 2 is shown in general terms in Table 3. Each unique combination has been listed pictorially and labelled with the shorthand notation of Structure 2 defined above.
TABLE 3

TABLE 3-continued

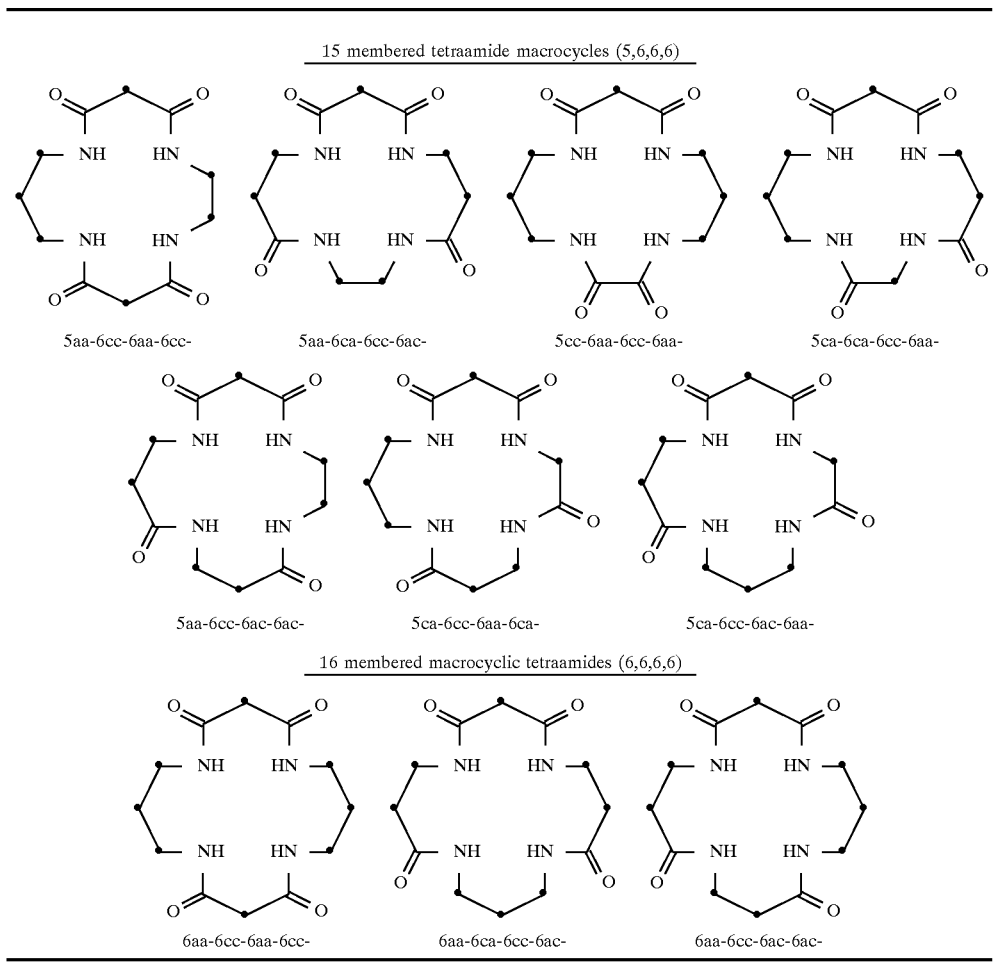

The individual Bridge, Arm and Linker starting materials can either be obtained commercially or synthesized by standard techniques. Examples of syntheses for a few non-commercially available starting materials are provided herein and in the Experimental Section. A powerful alternative route for the preparation of substituted and unsubstituted malonates has been reported by A. P. Krapcho, E. G. E. Jahngen, Jr. and D. S. Kashdan. "α-carbalkoxylations of carboxylic acids. A general synthetic route to monoesters of malonic acids", Tet. Lett. 32, p. 2721–2723 (1974). The oxidatively robust macrocyclic tetraamides shown in Table 3 may be used to synthesized without having to resort to the use of species that contain high energy N-N bonds, such as axides, hydrazines and azo constituents.

Schematics 1 to 3 below pictorially demonstrate substitution at the variable positions shown by a ● in Table 3. The remainder of this section discusses how to choose R substituents in general terms, and lists some representative examples of substituted Bridge, Arm and Linker starting materials in tabular form.

Single Node Substitution

Starting materials containing only one variable position are substituted by a carbon atom bearing two R groups, a —C($R_a$) ($R_b$)— unit, (in this context the dashes (—) refer to single bonds as opposed to amide bonds).

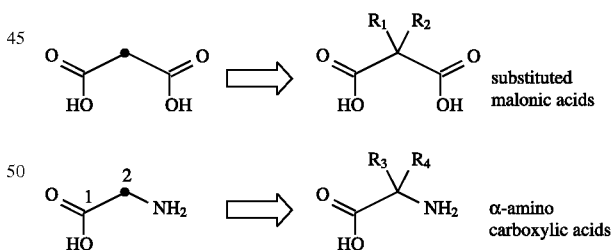

Schematic 1: Replacement of a single variable position is always by a —C($R_a$)($R_b$)— unit.

For substitution at any single variable position the R groups on the —C($R_a$) ($R_b$)— unit may be the same or different and are selected from the group consisting of hydrocarbons and heteroatom (e.g., halogen, N, O, Si, P, S) substituted hydrocarbons. Specific choices for the R groups other than $R_1$ and $R_2$ are from the following types/subtypes either singly or in combination (e.g. for R=arylsilylester, only aryl, esters and siloxanes are listed); H, ketones, aldehydes, carboxylic acids, hidden or protected/activated carboxylic acids (see Table 1), esters, ethers, amines, hidden or protected/activated amines (see Table 1), imines, amides, nitro, sulphonyls, sulfates, phosphoryls, phosphates, silyl, siloxanes, alkyl, alkenyl, alkynyl, halo, aryl, and compounds chosen from biological systems e.g. natural or unnatural amino acid sidechains, heterocyclic rings, lactams, lactones, alkaloids, terpenes (steroids, isoprenoids), lipid or phospholipid chains.

For single node substitution, fusion of the $R_a$ and $R_b$ groups at a position that is not the site of substitution, but α to the site of substitution yields a species doubly bonded to the node such as an oxo (=O), imine (=$NR_a$), or a substituted vinyl group (=$CR_aR_b$). Formation of imines or substituted vinyl groups constitutes a form of nodal migration. If the original $R_a$ and $R_b$ groups are fused at a site that is not the site of substitution and is not α to the site of substitution then a cyclic ring structure is formed. If such cyclic groups are formed, additional R substituents on the cyclic groups are chosen in the same manner as for normal single node or multi node substitution (including the possibility of further R group fusions at one or more nodes to yield additional oxo, imine, substituted vinyl groups, or spiro, benzo, substituted benzo, heterocyclic, substituted heterocyclic, cycloalkyl, substituted cycloalkyl, cycloalkenyl or substituted cycloalkenyl ring structures). Preferred spiro/cyclic ring sizes are four-, five- or six-membered rings.

Multi Node Substitution

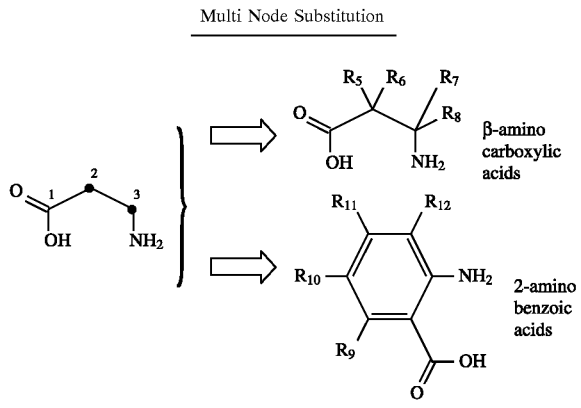

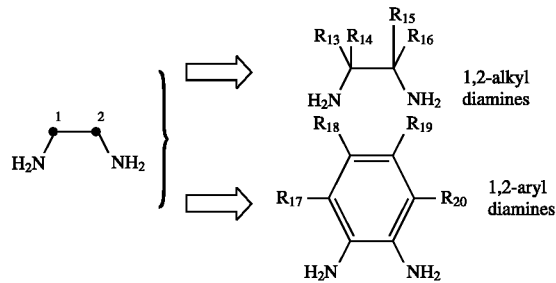

Schematic 2: Replacement at two variable positions can be by two —$C(R_a)(R_b)$— units or the two variable positions can be combined to make up part of an aryl or heterocyclic ring structure.

For multiple node substitution individual —$C(R_a)(R_b)$— positions are substituted identically as for single node substitution (see above). In addition to the types of substitution found for single nodes, it is also possible to combine or connect multiple nodes together via fusion of the R groups located on different nodes at sites that either are (combination), or are not (connection), the sites of attachment. Combination of sites that are adjacent leads to ethylenic units (—$C(R_a)$=$C(R_b)$—) a form of R group elimination. Connection of nodes via R group fusion at sites that are not the points of attachment or combination of sites that are not adjacent leads to the formation of cyclic structures, such as spiro, benzo, substituted benzo, heterocyclic, substituted heterocyclic, cycloalkyl, substituted cycloalkyl, cycloalkenyl or substituted cycloalkenyl ring structures. Five- and six-membered rings are preferred.

If cyclic groups are formed, or if there are residual R groups remaining from combination at adjacent sites, the residual R groups and the substituents on the cyclic groups are chosen in the same manner as for normal single node or multi node substitution (including the possibility of further R group fusions to yield additional spiro, benzo, substituted benzo, heterocyclic, substituted heterocyclic, cycloalkyl, substituted cycloalkyl, cycloalkenyl or substituted cycloalkenyl ring structures).

An important point is that the definitions for both single node and multi node substitution can function recursively, e.g. substituted o-phenylene diamine=>substituted heterocyclic o-phenylene diamine=>substituted spiro-cycloalkyl heterocyclic o-phenylene diamine etc.

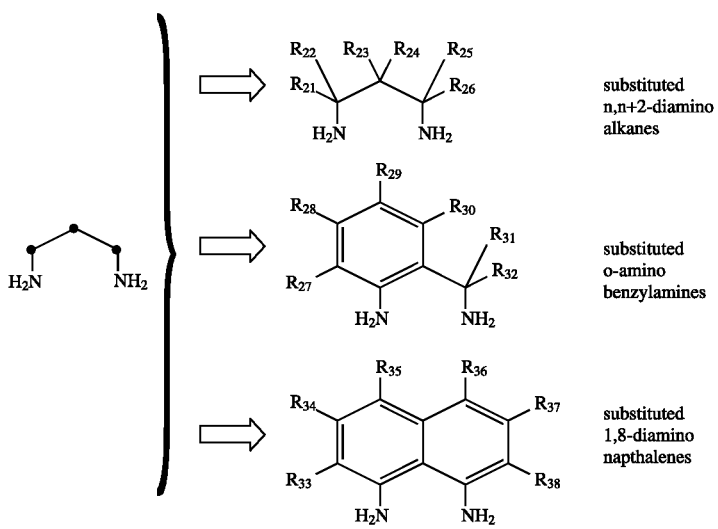

Schematic 3; Replacement at three variable positions can either be by three —C($R_a$)($R_b$)— units or two of the variable positions can be combined to make up part of an aryl or heterocyclic ring structure with the third position being replaced by a —C($R_a$)($R_b$)— unit or the three variable positions can all be combined to form part of a fused diaryl, fused aryl heterocyclic, or fused diheterocyclic ring structure.

Some representative examples of commercially available land/or synthetically versatile Linker, Arm and Bridge starting materials are shown in Tables 4, 5 and 6, respectively. A macrocyclic tetraamido compound having the desired chelate ring configuration shown in Table 3, i.e., 5556, 5566, 5656, 5666 or 6666, and variations thereof, can be constructed by reference to the general choice and combination of starting materials for various chelate configurations shown in Table 2, i.e., parent, protected/activated or hidden, followed by the choice of the specific starting materials from Tables 4, 5 and 6. Use of those functionally and similar starting materials in the new synthetic method will provide a macrocyclic tetraamido compound having a chelate ring configuration and substituent array suited to a particular end use. The symbol * in the Tables indicates a substituent that is comparatively robust towards oxidation. The symbol † in the tables indicates substituents that are very oxidatively robust.

Table 4 identifies some representative dicarboxylic acid malonate derivatives, i.e. Linkers, of interest for the preparation of macrocyclic tetraamides, either in parent, hidden, or protected/activated forms.

TABLE 4

The Malonates

Derivatives of Oxalic Acid (5 cc)

| Registry # | Compound Name | | |
|---|---|---|---|
| | *Oxalyl Chloride | | |

Derivatives of Malonic Acid (6 cc)

| Registry # | Compound Name | Registry # | Compound Name |
|---|---|---|---|
| Disubstituted malonates | | | |
| 31696-00-1 | *Diethyl butylethylmalonate | | *Diethyl di-n-octylmalonate |
| 00596-76-9 | *Diethyl butylhexylmalonate | 24251-93-2 | *Diethyl di-n-pentylmalonate |
| 00083-27-2 | *Diethyl butylmethylmalonate | | *Diethyl di-2-propenyl malonate |
| | *Diethyl butylethylmalonate | 03195-24-2 | *Diethyl di-n-propylmalonate |
| | *Diethyl butylpentylmalonate | | *Diethyl ethylheptyl malonate |
| | *Diethyl butylpropylmalonate | | *Diethyl ethylhexylmalonate |
| | *"2,2-Diethylbutyric acid" | 00133-13-1 | *Diethyl ethyl(1-methylbutyl) malonate |
| 18719-43-2 | *Diethyl "1,1-cyclobutane dicarboxylate" | | *Diethyl ethylmethylmalonate |
| 53608-93-8 | *Diethyl "1,1-cyclopropane dicarboxylate* | 02049-70-9 | *Diethyl ethyl(1-methyl propyl)malonate |
| 01559-02-0 | *Diethyl decylethylmalonate | | *Diethyl ethylnonylmalonate |
| 05077-96-3 | *Diethyl decylmethylmalonate | 05408-35-5 | *Diethyl ethyloctylmalonate |
| | *Diethyl diallylmalonate | 00076-67-5 | *Diethyl ethylpentylmalonate |

TABLE 4-continued

The Malonates

| | | | |
|---|---|---|---|
| 00597-55-7 | *Diethyl di-n-butylmalonate | | *Diethyl ethylphenylmalonate |
| 00596-75-8 | *Diethyl di-n-decylmalonate | 71691-56-0 | *Diethyl ethylpropylmalonate |
| | *Diethyl diethylmalonate | | *Diethyl methyl(2-methyl butyl)malonate |
| | *Diethyl di-n-heptylmalonate | | *Diethyl methyl(2-methyl propyl)malonate |
| | *Diethyl di-n-hexylmalonate | 34009-61-5 | *Diethyl methylnonylmalonate |
| | †Diethyl dimethylmalonate | 01575-67-3 | †Diethyl methylphenylmalonate |
| 01619-62-1 | *Diethyl di-n-nonylmalonate | 58447-69-1 | *Diethyl methylpropylmalonate |
| | *"1,1-cyclopropane dicarboxylate" | 00083-27-2 | *Diethyl methyl-iso-propylmalonate |
| | *"1,1-cyclopentane dicarboxylate" | | *"1,1-cyclobutane dicarboxylate" |
| | †ditrifluoromethyl malonic acid | | *"1,1-cyclohexane dicarboxylic" |
| | †difluoro malonic acid | | †ditrifluoroethyl malonic acid |
| | | | †dichloro malonic acid |

Table 5 identifies some representative α and β amino carboxylic acids, i.e. Arms, of interest for the preparation of macrocyclic tetraamides, either in parent, hidden, or protected/activated form.

TABLE 5

The Amino Carboxylic Acids

Derivatives of α-Amino Carboxylic Acids (5 ac)

| | |
|---|---|
| *R(−)-2-amino-2-methyl butanedioic acid | *S(−)-2-amino-2-methyl-4-pentenoic acid monohydrate |
| *S(+)-2-amino-2-methyl butanedioic acid | *2-amino-2-norbornane carboxylic acid |
| *S(+)-2-amino-2-methyl butanoic acid hydrate | *R(−)-2-amino-2-phenylbutyric acid |
| *2-amino-2-methyl butyric acid | *1-aminocyclopropane-1-carboxylic acid |
| *2-amino-2-methyl glutaric acid | *1-aminocyclobutane-1-carboxylic acid |
| *R(−)-2-amino-2-methyl-3-hydroxy propanoic acid | *1-aminocyclopentane-1-carboxylic acid (cycloleucine) |
| *S(+)-2-amino-2-methyl-3-hydroxy propanoic acid | *1-aminocyclohexane-1-carboxylic acid |
| *(S)-2-amino-2-methyl-4-phosphonobutanoic acid | *S(+)-2-amino-2-methyl-3-phenyl propanoic acid |
| †α,α-diphenyl glycine | †α-phenyl alanine ((+/−)α-methyl-α-phenyl glycine) |
| †α-amino-isobutyric acid (α-methyl alanine) | *S(+)-2-amino-2-phenylbutyric acid |
| *cis-1-amino-3-(2-phosphonoacetyl) cyclobutane-1-carboxylic acid | |

Derivatives of β-Amino Carboxylic Acids (6 ac)
*†The β amino acids derived from 2-amino-benzoic acid (anthranilic acid) are quite oxidatively robust

| Registry # | Compound containing 2-amino-benzoic acid | Registry # | Compound containing 2-amino-benzoic acid |
|---|---|---|---|
| 118-92-3 | †(o-amino-benzoic acid, anthranilic acid) | 118-92-3 | †(o-amino-benzoic acid, anthranilic acid) |
| 619-17-0 | †4-nitro- | 3177-80-8 | *3-methoxy- |
| 616-79-5 | †5-nitro- | 6705-03-9 | *5-methoxy- |
| 4389-45-1 | *3-methyl- | 394-31-0 | *5-hydroxy- |
| 2305-36-4 | *4-methyl- | 4920-81-4 | *3-hydroxy-hydrochloride |
| 2941-78-8 | *5-methyl- | 446-32-2 | †4-fluoro- |
| 4389-50-8 | *6-methyl- | 446-08-2 | †5-fluoro- |
| 609-86-9 | *3,5-diiodo- | 434-76-4 | †6-fluoro- |
| 5653-40-7 | *4,5-dimethoxy- | | *4-chloro-5-sulfamoyl- |
| 50419-58-4 | *3,4-dimethyl- | 6388-47-2 | †3-chloro- |
| 14438-32-5 | *3,5-dimethyl- | 89-77-0 | †4-chloro- |
| 15540-91-7 | *3,6-dimethyl- | 635-21-2 | †5-chloro- |
| 2789-92-6 | †3,5-dichloro- | 2148-56-3 | †6-chloro- |

TABLE 5-continued

The Amino Carboxylic Acids

| | | | |
|---|---|---|---|
| 609-85-8 | *3,5-dibromo-<br>*3,5-dibromo-6-fluoro- | 1765-42-0<br>61948-85-4 | †3-bromo-5-methyl-<br>†3,4,5,6-tetrafluoro-<br>*3,4,5-trimethoxy- |

| Registry # | Other β-amino<br>carboxylic acids | Registry # | Other β-amino<br>carboxylic acids |
|---|---|---|---|
| | | 5959-52-4 | †3-amino-2-napthoic acid |
| 5434-20-8 | *3-amino-phthalic acid | 5345-47-1 | *2-amino-nicotinic acid<br>(2-aminopyridine-3-<br>carboxylic acid) |
| 614-19-7 | *β-amino-hydrocinnamic<br>acid(D,L-3-amino-3-<br>phenyl-propionic acid) | 82-24-6 | †1-amino-anthraquinone-2-<br>carboxylic acid |
| 52834-01-2 | *2-amino-4,6-dimethyl-3-<br>pyridinecarboxylic acid<br>hydrochloride | 1664-54-6 | *3-amino-3-phenyl-<br>propionic acid |
| 54711-21-6 | *5-amino-4-cyano-1-methyl-<br>pyrazole | 50427-77-5 | *5-amino-1-phenylpyrazole-<br>4-carboxamide |
| 698-29-3 | *4-amino-5-cyano-2-methyl<br>pyrimidine | 72-40-2 | *5(4)-aminoimidazole-4(5)-<br>carboxylate hydrochloride |
| | *4-amino-5-cyano-2-methoxy<br>pyrimidine | 68302-09-0 | *2-amino-7-ethyl-5-oxo-5H-<br>[1]benzopyrano[2,3-<br>b]pyridine-3-carbonitrile |
| 41680-34-6 | *3-aminopyrazole-4-<br>carboxylic acid | 22603-53-8 | *2-amino-3,5-<br>dinitrobenzonitrile |
| 87550-19-4 | *3,6-dinitrophthalic acid<br>pyridine salt | | *5-amino-4-cyano-1-(4-<br>chlorophenyl)pyrazole |
| 5424-01-1 | *3-amino pyrazine-2-<br>carboxylic acid | | *5-amino-4-cyano-1-(4-<br>nitrophenyl)pyrazole |
| 10312-55-7 | *2-amino terephthalic acid | 16617-46-2<br>6375-47-9 | *5-amino-4-cyano-pyrazole<br>*3-amino-4-acetamido<br>anisole |

Table 6 identifies some representative diamines, i.e. Bridges, of interest for the preparation of macrocyclic tetraamides, either in parent, hidden, or protected/activated forms. Amine and protected/activated or hidden amine functionalities are used interchangeably.

TABLE 6

The Diamines

Derivatives of 1,2-Aryl Diamines (5 aa)
*†all of the aryl diamines shown are comparatively robust towards oxidation.

| Registry # | Compound containing<br>o-Phenylenediamine | Registry # | Compound containing<br>o-Phenylenediamine |
|---|---|---|---|
| 95-94-5 | Substituents = 0<br>†(1,2-Benzenediamine)<br>No. of Unique<br>Substituents = 1 | 95-54-5 | Substituents = 0<br>†(1,2-Benzenediamine)<br>No. of Unique<br>Substituents = 1 |
| 18645-88-0 | †3-fluoro- | 21745-41-5 | †3-chloro- |
| 367-31-7 | †4-fluoro- | 95-83-0 | †4-chloro- |
| 153505-39-6 | †3,4-difluoro- | 1668-01-5 | †3,4-dichloro- |
| 2369-29-1 | †3,5-difluoro- | 5233-04-5 | †3,5-dichloro- |
| 2369-30-4 | †3,6-dichloro- | 21732-93-4 | †3,6-dichloro- |
| 76179-40-3 | †4,5-difluoro- | 5348-42-5 | †4,5-dichloro- |
| 168966-54-9 | †3,4,5-trifluoro- | 30064-28-9 | †3,4,5-trichloro- |
| 363-74-6 | †3,4,6-trifluoro- | 1962-10-3 | †3,4,6-trichloro- |
| 2993-07-9 | †3,4,5,6-tetrafluoro- | 877-12-3 | †3,4,5,6-tetrachloro- |
| 1575-36-6 | *3-bromo- | 34446-43-0 | *3-iodo- |
| 1575-37-7 | *4-bromo- | 21304-38-1 | †4-iodo- |
| 1575-38-8 | *3,5-dibromo- | 144793-03-3 | *3,6-diiodo- |
| 69272-50-0 | *3,6-dibromo- | 76179-43-6 | *4,5-diiodo- |
| 49764-63-8 | *4,5-dibromo-<br>No. of Unique<br>Substituents = 2 | | No. of Unique<br>Substituents = 2 |
| 75293-95-7 | *4-bromo-5-chloro- | 132915-81-2 | †3-chloro-4-fluoro- |
| 16429-44-0 | *5-bromo-3-chloro- | 153505-33-0 | †3-chloro-5-fluoro- |
| 172215-94-0 | *3-bromo-4,5-dichloro- | 139512-70-2 | †4-chloro-5-fluoro- |
| 98138-54-6 | *4-bromo-3,5-dichloro- | 153505-43-2 | *5-chloro-3-iodo- |

TABLE 6-continued

The Diamines

| | | | |
|---|---|---|---|
| 74908-80-8 | *3,5-dibromo-4-chloro- | 153505-34-1 | †3-chloro-4,5-difluoro- |
| 115440-10-3 | *3-bromo-5-fluoro- | 170098-84-7 | †4-chloro-3,5-difluoro- |
| 153505-37-4 | *4-bromo-5-fluoro- | 156425-14-8 | †4-chloro-3,5,6-trifluoro- |
| 153505-35-2 | *3-bromo-4,5-difluoro- | 153505-47-6 | *4,5-dichloro-3-iodo- |
| 156425-12-6 | *4-bromo-3,5,6-trifluoro- | 18225-92-8 | †3,4,6-trichloro-5-fluoro- |
| | | 153505-45-4 | *5-fluoro-3-iodo- |

| Registry Number | Additional 1,2-Benzenediamines | Registry Number | Additional 1,2-Benzenediamines |
|---|---|---|---|
| | *4,5-dimethyl- | | *4-methyl- |
| | †4,5-dinitro- | | †4-nitro- |
| 88580-71-6 | *4,5-dimethoxy | | *4-methoxy- |
| | *4,5-diamino- | | *4-amino- |
| | †4,5-diacetamido- | | †4-acetamido- |
| | †4,5-ditrifluoromethyl- | | †4-trifluoromethyl- |
| | †4,5-dicyano- | | †4-cyano- |
| | *4.5-dihydroxy | 615-72-5 | *4-hydroxy(3,4-diamino-phenol) |
| | | 59649-56-8 | *3-hydroxy(2,3-diamino-phenol) |

| | Other n,n + 1-Diamines | | Other n,n + 1-Diamines |
|---|---|---|---|
| | †1,1,2,2,-tetramethyl | 452-58-4 | *2,3-diamino pyridine |
| 7598-26-7 | *2-amino-3-nitro-5-methyl pyridine | 54-96-6 | *3,4-diaminopyridine |
| 6635-86-5 | *2-amino-3-nitro-4-picoline(2-amino-4-methyl-3-nitro pyridine) | | *2-amino-3-nitro-5-bromo-pyridine |
| 82039-90-5 | *5-amino-4-nitro-imidazole | | *4-amino-5-nitro-6-chlor-pyrimidine |
| | *5-amino-3-methyl-4-nitro-isoxazole | | *2-amino-3-nitro-9-fluorenone |
| | *5-amino-1,3-dimethyl-4-nitro-pyrazole | 7598-26-7 | *2-amino-3-nitro-5-methyl-pyridine |
| 6632-68-4 | *6-amino-1,3-dimethyl-5-nitroso-uracil | | *4-amino-5-nitroso-uracil |
| 22603-53-8 | *2-amino-3,5-dinitro-benzonitrile | 1672-48-6 | *6-amino-5-nitroso-2-thio-uracil |
| 3531-19-9 | *1-amino-2,4-dinitro-6-chlorobenzene | | *2-amino-5-bromo-3-nitro-pyridine |
| 5442-24-0 | *4-amino-2,6-dihydroxy-5-nitro-pyrimidine | 33685-60-8 | †9,10-dinitro-anthracene |
| | *4-amino-2,6-diketo-1,3-dimethyl-5-nitroso-pyrimidine | | *6,7-dinitro-2,3-diphenoxy-quinoxaline |
| | *1,2-dinitro-tetramethyl-benzene | 35975-00-9 | †5-amino-6-nitro-quinoline |
| | *cis-1,2-diamino-1,2- | 771-97-1 | †2,3-diamino-naphthalene |
| | *cis-1,2-diamino-1,2-dimethyl-cyclopentane | 938-25-0 | †1,2-diamino-naphthalene |
| 36023-58-2 | †5,6-diamino-2,3-dicyano-pyrazine | 39070-63-8 | *3,4-diamino-benzophenone |
| 5440-00-6 | *5,6-diamino-1,3-dimethyl-uracil | 68836-13-5 | †6,7-dinitro-quinoxaline |
| | *5,6-diamino-3-methyl-uracil | | *5,6-dinitro-quinoxaline-2,3-dione |
| 1758-68-5 | †1,2-diaminoanthraquinone | 2379-57-9 | *6,7-dinitro-quinoxaline-2,3-dione |
| 6968-22-5 | *3-amino-4-nitro-benzoic acid | 52057-97-3 | *3,4-diamino-5-hydroxy-pyrazole sulfate |
| 13754-19-3 | †4,5-diamino-pyrimidine | 1672-50-0 | *4,5-diamino-6-hydroxy-pyrimidine |
| 3240-72-0 | *4,5-diamino-uracil (5,6-diamino-uracil) | | |

| | Derivatives of n,n + 2 Diamines (6 aa) | | |
|---|---|---|---|
| Registry # | n,n + 2-diamines | Registry # | n,n + 2-diamines |
| | *2-amino-2-(2-aminophenyl)-propane | | †2,4-diamino-2,4-dimethyl-pentane-3-one |

TABLE 6-continued

The Diamines

| | *1,3-diamino-1,3-dimethylcyclohexane | *2,4-diamino-2,4-dimethylpentane |
|---|---|---|
| 479-27-6 | †1,8-diaminonaphthalene | |

The list of n, n+2-Diamines is significantly shorter than for the other derivatives, in large part because the syntheses of the required n,n+2 diamines are more complex than for the n, n+1 diamines.

Some specific examples of bridge, arm and linker starting materials are shown in Table 7. In each case the amide bonds have been retrosynthetically decomposed to form an amine equivalent (amine, nitro, azide, isocyanate, etc. see Table 1) and a carboxylic acid equivalent (acid, ester, acyl chloride, nitrile etc. see Table 1).

The bridges and linkers of Table 7 conserve local two fold symmetry while all of the arms shown lead to 5-membered chelate rings.

TABLE 7

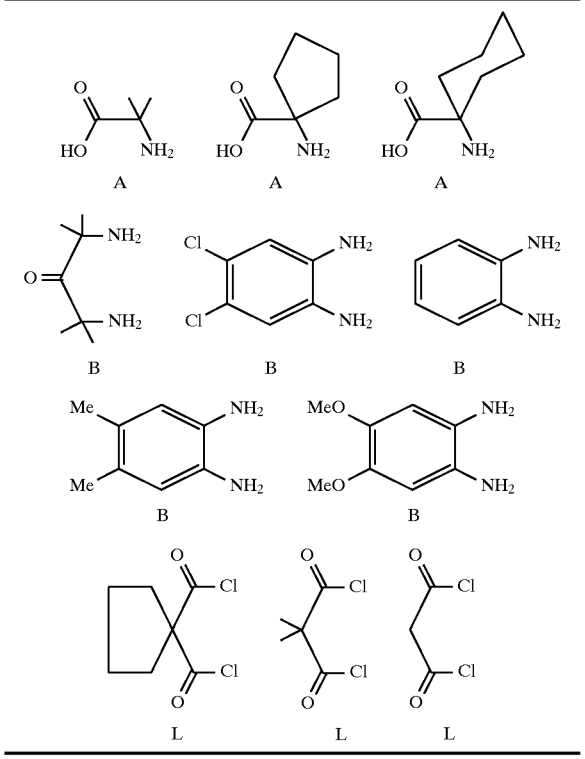

Some specific Bridge, B, Arm, A, and Linker, L, starting materials.

The R groups do not participate in the synthesis reaction to numerous variations are possible. However, as discussed above, to form the oxidatively robust compound and catalyst, there are certain restrictions placed on the R groups. There is considerable evidence that hydrogen atom abstraction occurs between the linker's R substituents and the axial ligand bound to the central metal atom of the ultimate chelate system. This abstraction then is believed to lead to oxidative degradation, as shown in the proposed mechanism of FIG. 1. Molecular models revealed that, in a boat conformation of the macrocyclic complex's six-membered linker ring, the methylene H-atoms of the ethyl groups can reach to the oxygen atom of an Fe-oxo complex. This and other data lend support to the mechanism shown in FIG. 1 and explain the parameters of the $R_1$ and $R_2$ substituents. To avoid the H-atom abstraction and consequent degradation, the R groups of the preferred macrocyclic compounds should be those that will slow down the H-atom abstraction reaction and thereby slow down oxidative degradation. To accomplish this, the $R_1$ and $R_2$ groups of the compound of the present invention are those that have a good bond strength, are unreactive, or which are not accessible to the axial ligand, such as sterically or conformationally hindered groups. Any one or any combination of these attributes may be employed. The latter option can be achieved by reducing the conformational freedom of the $R_1$ and $R_2$ groups so that they simply are not close enough to react. As used herein good C-H bond strength means more than 94 Kcal.mol$^{-1}$ more than 85 Kcal.mol$^{-1}$ for sterically inaccessible C-H bonds.

The malonate linker portion is the most sensitive part of the macrocycle ligand. Preferred R groups on the linker include methyl, halogen, hydrogen, $CF_3$ and a spiro-cyclopentyl or spiro-cyclohexyl ring in place of $R_1$ and $R_2$.

There is considerably more freedom in choosing the R substituents for the arm portions than for the linker because of the robustness of this portion of the compound which may reflect the inability of a five-membered ring to adjust to bring oxidizable C-H groups in contact with an axial oxo ligand. Thus, the R groups of the α and β amino carboxylic acid can also be chosen to tailor the substituents of the resulting macrocycle to the desired end use. The macrocycle may be symmetrical or asymmetrical. For asymmetrical macrocycles, two different amino acid starting materials are used and the resulting macrocycles are a mixture of symmetrical and asymmetrical versions. The two versions can be separated by known separation techniques. A few examples of the compounds of the present invention are shown below.

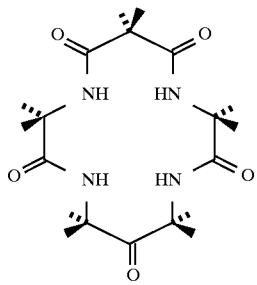

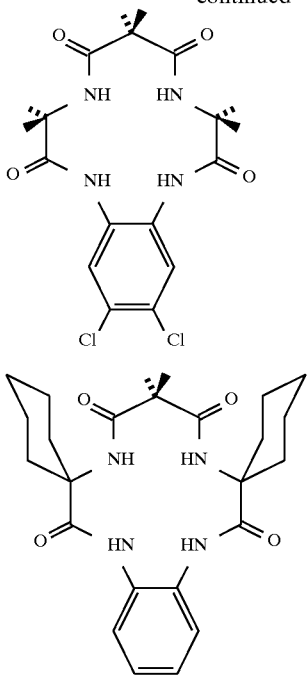

Once the macrocyclic tetradentate ligand has been prepared, the macrocyclic compound may be complexed with a wide range of metal ions, preferably a transition metal, and most preferably a group 6, 7, 8, 9, 10 or 11 transition metal, to form a chelate complex of the formula

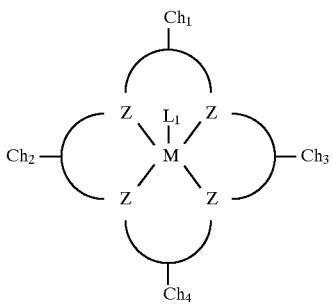

wherein M is the metal, Z is an oxidation resistant metal-complexing atom, such as N or O, $L_1$ is any labile ligand, $Ch_1$, $Ch_2$, $Ch_3$ and $Ch_4$ are oxidation resistant components of the chelate system described above which are the same or different and which form five- or six-membered rings with the adjacent ZMZ atoms.

Complexation is achieved by the following method. The, macrocyclic ligand is dissolved in a supporting solvent, usually THF, and deprotonated by treatment with a base, preferably lithium bis-trimethylsilylamide, lithium di-isopropyl amide, t-butyl lithium, n-butyl lithium, or phenyl lithium. Any base that removes the protons at the metal complexing site, i.e., the amide N-H protons of a tetraamido compound, will suffice. Noncoordinating organic soluble bases are preferred. After the ligand is deprotonated, a metal ion is added. The resulting intermediate, a comparatively low valent ligand metal species, is then oxidized. The oxidation step is preferably performed with air, chlorine, bromine, or benzoyl peroxide to produce the metal chelate complex usually as a lithium salt. Metathesis of the resulting complex to form a tetraalkyl ammonium, tetraphenyl phosphonium or bis(triphenylphosphoranylidene) ammonium (PPN) salt tends to yield metal chelate complexes that are easier to purify as compared to the lithium ion containing complexes. The purified metal chelate complex, can then be used to catalyze oxidation reactions.

If the complex is then combined with a strong O-atom transfer oxidant, preferably a peroxide, such as hydrogen peroxide, t-butyl hydroperoxide, cumyl hydroperoxide or a peracid, a ligand metal IV, V or VI oxo intermediate is produced. When oxidatively robust substituents have been employed to generate the ligand framework, the robust, high oxidation state oxo containing species apparently form as reactive intermediates. It is believed that these high valent oxo containing species are the active transfer agents in catalyzing a number of oxidation reactions.

When a low valent metal species is exposed to a peroxide or other [O] containing oxidant the metal attracts and binds the oxygen from the oxidant. Depending on the metal, the bond between the metal and the oxygen will be very strong or may be only strong enough to remove the oxygen from the oxidant for subsequent transfer to another constituent.

If the metal is a metal III ion, the resulting oxo species will in general be a metal V ion. If the metal is a metal IV ion, the resulting oxo species will in general contain a metal VI ion or a metal V complex with a second oxidation site on the ligand, i.e., a ligand cation-radical. The combined stabilizing effect of the macrocyclic ligand and the participation of the d electron count at the metal center in controlling the degree of bonding to an oxo ligand tends to favor early transition metal complexes forming very strong oxygen-metal bonds to yield stable oxides. The middle and later transition metals tend to remove the oxygen from the oxidant and bind the oxo ligand to form a reactive intermediate. In the metal ligand system produced by the new synthetic method, the middle and later transition metals tend to promote the transfer of oxygen.

In addition to its stabilizing effect, the ligand also exerts influence on the metal properties. By controlling the metal, the electron density of the macrocycle, the charge on the complex, and the bond strength/bond order to the coordinated oxo ligand, the metal ligand complex can be fine tuned to achieve a complete range of oxygen transfer abilities, from stable oxides to high valent oxidation catalysts.

In the preferred embodiment, the axial ligand, $L_1$, is labile because it occupies its position relative to the metal until the chelate system is introduced into a solution containing an oxidant. The labile ligand will dissociate and will be replaced by the oxidant, most generally an O-atom transfer agent, but also any general oxidant that can serve to activate the metal ion to perform catalysis. Preferred labile ligands include, but are not limited to, the $Cl^-$ anion, halide ions in general, $CN^-$, $H_2O$, $OH^-$, ROH, $NH_3$, or any amine, carboxylate, phenol or phenoxide, pyridine, ether, sulfoxide, ketone, or carbonate. The oxidation site in the metal complexes of aromatic-ring containing macrocycles can be manipulated by the choice of axial ligands as well as by the ring substituents.

Macrocycles with spiro-cyclohexyl substituents have been prepared and found to render the macrocycle very hydrophobic and, remarkably, soluble in pentane and other light saturated aliphatic solvents. Long chain substituents, such as a dodecyl chain, or phospholipid chain will render the macrocycle soluble in membranes.

The spiro-cyclohexyl derivative is sterically hindered and has slower reaction rates than the other preferred substituents, so the normal synthesis of the amide intermediate of the first step of the method of the invention is altered.

Synthesis of the bis spiro-cyclohexyl macro linker intermediate was accomplished by adding acylating agent dropwise in multiple aliquots, preferably three, separated in time. Twelve hour intervals preferably followed by extended reaction periods produced the best results. Without the extended reaction periods, the yield was lower. The reaction sequence is shown in the sequences below. Cyclohexane can be used to separate the oxazalone form of the macro linker away from the other reaction products, or water can be added to hydrolyze the oxazalone in situ. Hydrolysis of the intermediate oxazalones provides an increased yield of the desired bis cyclohexyl macro linker product.

It has been observed that addition of an excess of the substituted malonyl dichloride improves the yield of macro linker with an optimum ratio of about 2 moles of amino acid to 1.35 to 1.5 moles of the substituted malonyl dichloride. The product mixture includes the macro linker and a mono-oxazalone form of the macro linker which can be readily hydrolyzed to yield additional product. The yield of the method is improved significantly if water is excluded from the reaction solution during ring closure reactions.

Pyridine diamines can also be utilized. The prior art azide synthetic route, which includes a reduction step that also

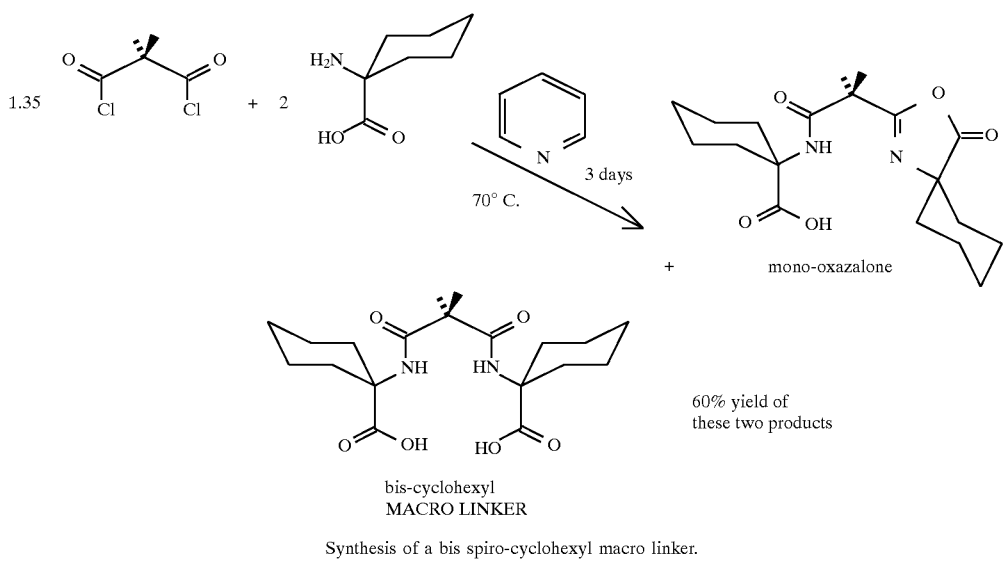

Synthesis of a bis spiro-cyclohexyl macro linker.

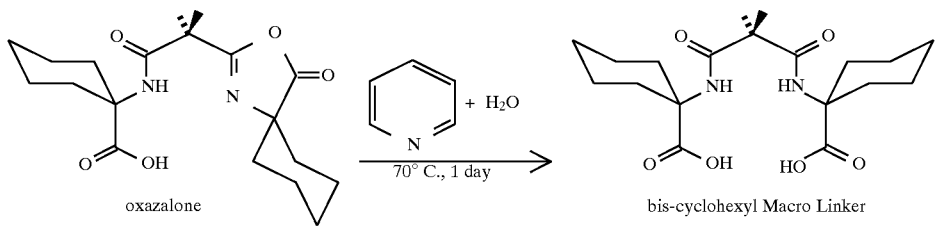

Hydrolysis of a hydrophobic oxazalone

The cyclohexyl-containing macro linker is then ready for ring closure in the same manner as other intermediates of the invention. However, due to the enhanced stability of the spiro-cyclohexyl containing macrocyclic intermediates, separation of the macrocycle from reaction by-products differs from other preferred ring closing constituents. Typically, the crude macrocyclic product is extracted into an organic solvent, such as $CH_2Cl_2$. The $CH_2Cl_2$ solution is washed with acids and bases to remove the impurities and side products that contain acidic and basic functionalities and to hydrolyze any oxazalone containing intermediates. The cyclohexyl tetraamido macrocycle is not well purified by the usual acid/base washes yielding instead an approximately 1:1 mixture of the bis cyclohexyl oxazalone and bis-cyclohexyl tetraamido macrocycle. Pentane extraction of the mixture yields a clean separation. The macrocycle is insoluble and isolated as a powder, while the pentane soluble fraction can be evaporated to yield large crystals of the bis cyclohexyl oxazalone.

reduces the pyridine ring, does not yield a macrocyclic compound having a pyridine bridge. Amino pendant variations would also be tedious to synthesize by the prior art synthesis methods. The amino pendant variations are of considerable interest because they permit the macrocyclic compound or metallocomplex to be tethered to a support, such as a polymer or sand, or to other molecules or substrates having functional groups which will covalently bond with the amine. Groups which covalently bond with amines are well known in the art and include in complexed form, for example, alkyl amines, amides, sulphonamides, imines, and other hidden or protected/activated forms, see Table 1.

The synthesis of the aryl amino pendant macrocycle proceeds generally as in Sequences 4 and 5.

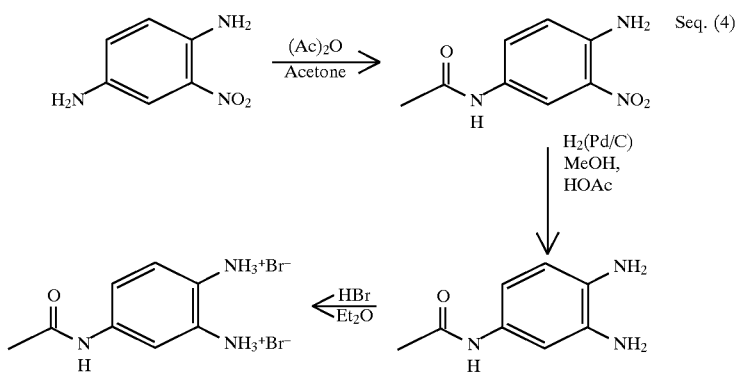

Synthesis of 1,2-Diamino-4-Acetamidobenzene (dihydrobromide)

The sequence includes the strategic and selective introduction of a protected amino group (an acetamide) onto the aryl diamine group (Bridge). The protected form of the bridge, an acetamido diamine is then suitable for ring closure via the standard diamine+intermediate linker synthetic routes described herein. An extended ring closure time is required to achieve macrocyclization and is attributed to unfavorable hydrogen bond formation between the attached oxazalone and the acetamido group, which would be expected to slow down the desired macrocyclization reaction.

Once the protected amino pendant macrocycle has been synthesized as in sequence 5, it can be metallated with cobalt. Removal of the acetyl protecting group then yields a macrocyclic cobalt complex that is ready to be attached to a support. Best results to date have been obtained by reacylating the pendant amino group with acryloyl chloride to yield an amide linked vinyl pendant macrocycle.

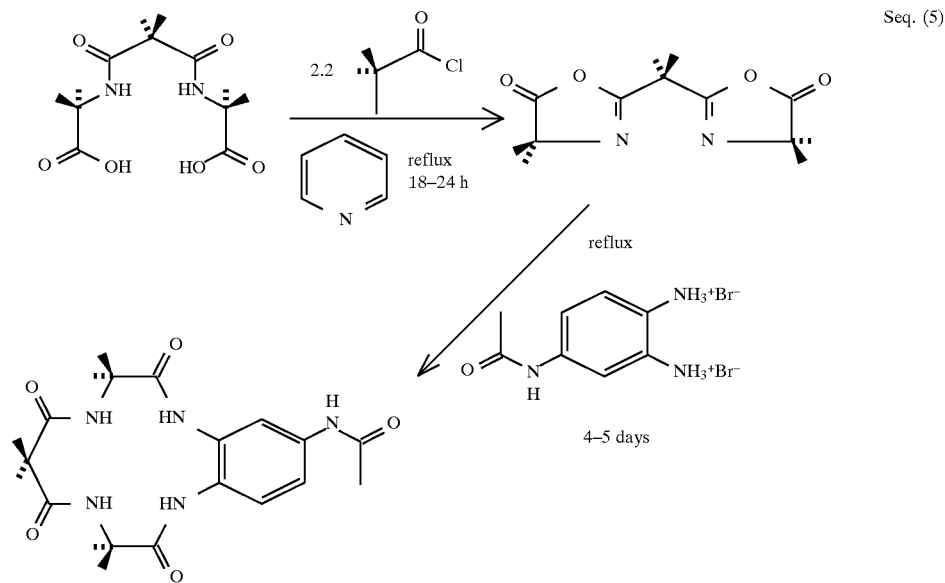

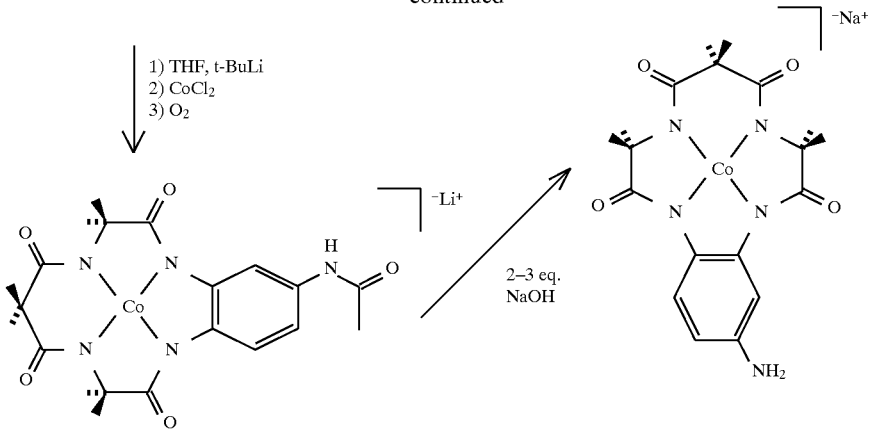

Synthesis of an amino pendant macrocyclic cobalt complex

Figure 5:
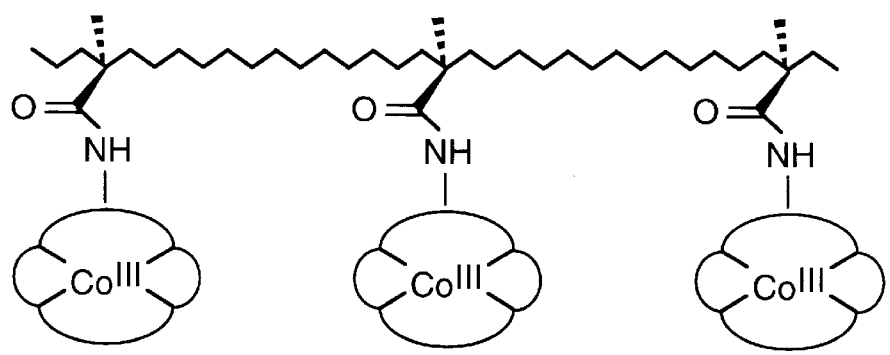
FIG. 5 is a schematic view of an amino pendant macrocycle metal complex covalently bound to a support surface.

This may then be copolymerized with a twenty fold excess of various acryloyl monomers to yield an acrylic polymer that contains a macrocyclic cobalt complex as a sidechain approximately every 20 residues, shown schematically in FIG. 5.

Figure 4:
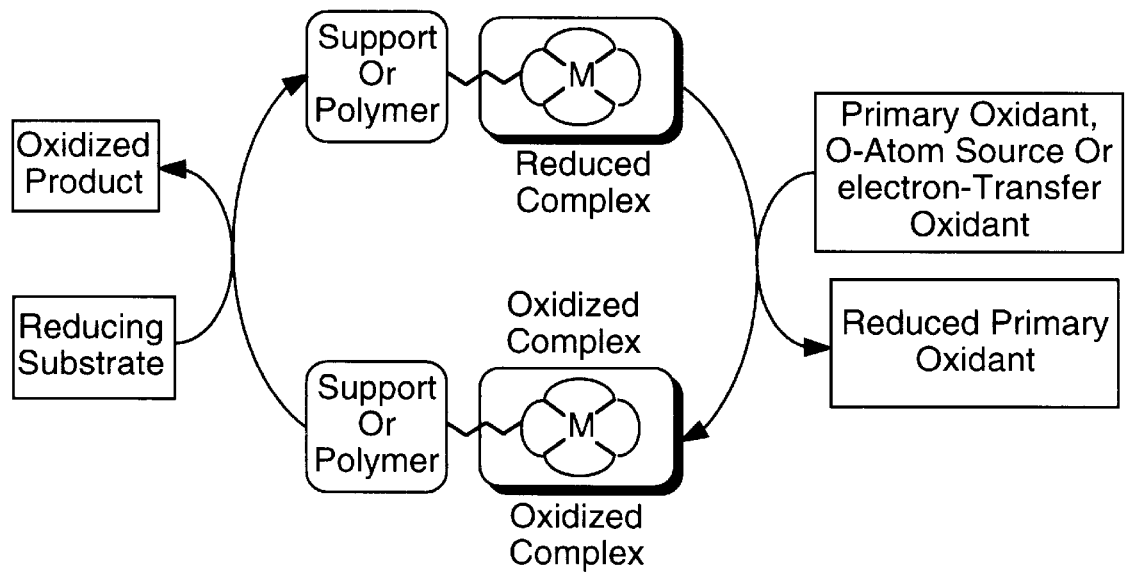
FIG. 4 is a view of a recyclable metallo-oxidant system.

By anchoring the macrocyclic metal complex to a polymer or some other support, the metal may be reclaimed and recycled according to the system shown schematically in FIG. 4. Environmentally toxic metals, for example $Cr^{VI}$ can be replaced by ore environmentally benign oxidation reagents, such as $Co^{IV}$ or $Co^{III}L^I$ species, where $L^I$ refers to a ligand centered oxidation.

Referring to FIG. 4, following the desired oxidation process, the anchored oxidant can be recycled via collection and reoxidation with a primary oxidant, such as hypochlorite, bromine or by electrolysis. Use of anchored macrocyclic metal species is expected to provide a viable method to significantly reduce the levels of discharge of toxic spent metallic species into the environment. The polymer bound oxidant system of FIG. 4 serves as an example of a recyclable "Green" oxidation reagent.

EXPERIMENTAL SECTION

Syntheses of Oxidatively Robust Tetraamido Ligands.

Materials. All solvents and reagents were reagent grade (Aldrich, Aldrich Sure-Seal, Fisher) and were used as received. Microanalyses were performed by Midwest Microlabs, Indianapolis, Ind.

Electrochemical Measurements. Cyclic voltammetry was performed under $N_2$ in a three compartment cell using a glassy carbon disk working electrode (A~0.0078 $cm^2$ or 0.071 $cm^2$), a Pt wire counter electrode, and a sodium chloride saturated calomel electrode (SSCE) as reference. $CH_2Cl_2$ (Aldrich Sureseal) or $CH_3CN$ (dried over $CaH_2$) were employed as solvents with a supporting electrolyte of $[Bu_4N][ClO_4]$ (0.1M, Fluka, vacuum dried 24 h ° C.) or $[Bu_4N][PF_6]$ (0.1M, Fluka puriss). A Princeton Applied Research Model 273 Potentiostat/Galvanostat controlled with a Compudyne 486DX computer was used and current/voltage curves were recorded on a Graphtec Model WX1200 X-Y recorder, or using a Princeton Applied Research Model 173/179 potentiostat/digital coulometer equipped with positive feedback IR compensation, a Model 175 universal programmer, and a Houston Instruments Model 2000 X-Y recorder. For some experiments, ferrocene (Fc) was added as an internal potential standard at the conclusion. Formal potentials were calculated as the average of anodic and cathodic peak potentials and are reported vs NHE. Peak-to-peak separation of the $Fc^+/Fc$ couple was similar to that of the iron compound couples in all cases. Plots of peak current vs. the square root of scan speed over the range 20–500 mV $s^{-1}$ were found to be linear for all couples.

Mass Spectrometry. Electrospray ionization mass spectra were acquired on a Finnigan-MAT SSQ700 (San Jose, Calif.) mass spectrometer fitted with an Analytica of Branford electrospray interface. Electrospray voltages of 2400–3400 V were utilized. Samples were dissolved in either acetonitrile or dichloromethane at concentrations of approximately 10 pmol/μl and were introduced into the ESI interface prior to data acquisition by direct infusion at a flow rate of 1 μl/min. Positive ion electron impact ionization (70 ev) MS experiments were performed on a Finnigan-MAT 4615 quadrupole mass spectrometer in conjunction with an INCOS data system. The ion source temperature was 150° C. and the manifold chamber temperature was 100° C. Sample introduction was by means of a gas chromatograph or a direct insertion probe. Positive ion fast atom bombardment mass spectra were acquired on a Finnigan-MAT 212 magnetic sector instrument in combination with an INCOS data system. The accelerating voltage was 3 kV and the ion source temperature was approximately 70° C. An Ion Tech saddle field fast atom gun was employed with xenon at 8 keV. Thioglycerol was utilized as the FAB matrix. Positive ion electron impact ionization (70 eV) MS/MS experiments were performed on a Finnigan-MAT TSQ/700 tandem quadrupole mass spectrometer. Sample introduction was by means of a direct insertion probe. The ion source was maintained at 150° C. and the manifold chamber was held at 70° C. Collision-induced dissociation (CID) was achieved by introducing argon into the center rf-only collision octapole until the pressure in the !manifold reached 0.9–2.5× $10^{-6}$ Torr. The nominal ion kinetic energy for CID product ions was <35 eV (laboratory reference). High resolution data were obtained on a JEOL JMS AX-505H double focusing mass spectrometer in the EB configuration using a resolution of 7500. Sample introduction was by means of a gas chromatograph or direct insertion probe. During mass spectral acquisition, perfluorokerosene was introduced into the ion source by means of a heated inlet. Exact mass assignments were obtained by computer-assisted interpolation from the masses of perfluorokerosene. GC/MS conditions: column, 20 m×0.25 mm DB-1701 (J & W Scientific); carrier gas, helium with a linear velocity of 40 cm/sec; injector, 125° C.; column temperature, 35° C. for 3 min, followed by an increase at 10° C./min to 100° C.; injection, split mode, appx. 50:1 ratio.

Spectroscopic Methods. 300 MHz $^1$H NMR spectra and 75 MHz $^{13}$C NMR spectra were obtained on an IBM AF300 instrument using an Oxford Superconducting magnet system, data acquisition was controlled by Bruker software. Infrared spectra were obtained on a Mattson Galaxy Series 5000 FTIR spectrometer controlled by a Macintosh II computer. UV/vis spectra were obtained on a Hewlett Packard 8452A spectrophotometer driven by a Zenith Z-425/SX computer. Conventional X-Band EPR spectra were recorded on a Bruker ER300 spectrometer equipped with an Oxford ESR-900 helium flow cryostat. Mössbauer spectra were obtained on constant acceleration instruments and isomeric shifts are reported relative to an iron metal standard at 298K. In order to avoid orientation of polycrystalline samples by the applied magnetic field, the samples were suspended in frozen nujol.

Syntheses of Diamines not Readily Available Commercially

Example 1

A. 1,2-Diamino-4,5-Dimethoxy Benzene from 1,2-Dimethoxy Benzene (veratrole)

1,2-Dinitro-4,5-Dimethoxy Benzene:

Veratrole was doubly nitrated according to the procedure of Drake et al, in "Synthetic Antimalarials. Some Derivatives of 8-Aminoquinoline", J. Amer. Chem. Soc., 1536, Vol. 68 (1946). Nitric acid (68.3 g, conc.) was added (dropwise, 1 h) to a well stirred solution of veratrole (48.3 g, 350 mmol, d=1.084) in glacial acetic acid (1450 mL) initially cooled to 15° C. The mixture needs to be held below 40° C. but above 10° C. by cooling and proper regulation of the rate of addition of the acid. Considerable mononitroveratrole separated out. Stirring was continued and additional nitric acid (212.7 mL, fuming) was added (dropwise, 1 h) while the temperature of the solution was held below 30° C. As the second nitration proceeded the mono nitroveratrole dissolved and when all the acid had been added, the solution was clear. The nitration mixture was allowed to stand for two hours and was then poured into ca. 1.5 L of ice/cold water. The precipitated dinitro compound was filtered, washed copiously with water until free from acid (pH>5), and recrystallized directly from a minimum of hot EtOH (600 mL). The yield of 1,2-Dimethoxy-4,5-dinitrobenzene was 69.0 g (87%). Characterization: m.p. 129.5°–130.5° C. $^1$H NMR (CDCl$_3$) δ [ppm]: 7.35 (s, 2H, ArH), 4.02 (s, 6H, OCH3). IR nujol ν [cm$^{-1}$]: 3124 (s, w, Aryl CH), 3073 (s, w, Aryl CH), 1592 (s, str, Aryl ring stretch), 1535 & 1518 (s, str, ArNO$_2$). Anal. Calcd. For C$_8$H$_8$N$_2$O$_6$: C, 42.11; H, 3.53; N, 12.28. Found: C, 42.12; H, 3.54; N 12.33.

112-Diamino-4.5-Dimethoxy Benzene:

1,2-Dimethoxy-4,5-dinitrobenzene (10 g, 43.8 mmol) was reduced to 1,2-Dimethoxy-4,5-diamino benzene in acidic MeOH (175 mL+2 eq. of mineral acid, (i.e., 10 mL of conc. HBr)) by catalytic hydrogenation using 10% Pd/C catalyst (24–36 h, 20–22 psi of H$_2$ was consumed from the reservoir). If more than 2 eq. of HBr are added initially the Pd/C catalyst is found to be strongly inhibited. After hydrogenation was complete an additional 4–5 eq. of conc. mineral acid was added to protect the material from aerial oxidation and the mixture rotary evaporated to yield a red/purple oil. The crude material was purified by adding a small volume of Abs. EtOH, then pouring the slurry into a 600 mL volume of ice cold Et$_2$O, with storage in the freezer overnight. The red-purple product was collected by filtration, air dried briefly then stored in a dessicator to complete the drying process. Prolonged exposure of the diamine salt to air/water causes a green color to develop which appears indicative of irreversible oxidation. Hydrogenation yield was ≈90%. Characterization of the red-purple 1,2-Dimethoxy-4,5-Diaminobenzene (dihydrobromide salt hydrate). $^1$H NMR (d$^5$ pyridine) δ [ppm]: 10.35 (s, br, 7.5 H, H$_2$O/py.HBr/R-NH$_2$ rapidly exchanging), 7.35 (s, 2 H, ArH), 3.60 (s, 6 H, ArOCH$_3$). IR (nujol/NaCl) ν [cm$^{-1}$]: 3085 (br, OH), 2557 (s, str, ArNH$_3$), 1623 (s, w, asymmetric NH$_3^+$ bend/Aryl ring stretch), 11539, 1519 (s, m. symmetric NH$_3^+$ bend). (Anal. Calcd. for C$_8$H$_{12}$N$_2$O$_2$) (HBr)$_2$ (H$_2$O)$_{0.66}$: C, 28.09; H, 4.52; N, 8.19. Found: C, 27.82; H, 4.18; N, 8.37. Independent confirmation of hydration was obtained from IR and NMR spectroscopy.

Preparation of the anhydrous sulfate salt of 1,2-Diamino-4,5-Dimethoxy Benzene has been reported by Nakamura, M. et. al. in "Fluorimetric Determination of Aromatic Aldehydes with 4,5-Dimethoxy-1,2-Diaminobenzene" Anal. Chim. Acta. (1982), 134, p.39–45 as follows: 1,2-Diamino-4,5-Dimethoxybenzene (2 g) was dissolved in EtOH (20 mL) and mixed with H$_2$SO$_4$ (conc., ca. 2 mL). The product was recrystallized from EtOH to almost colorless needles (yield ca. 2 g). Anal. Calcd for C$_8$H$_{14}$O$_6$N$_2$S: C, 36.1; H, 5.3; N, 10.5. Found: C, 35.85; H, 5.6; N, 10.4.

B. 1,2-Diamino-4-acetamidobenzene from 1,4-diamino-2-nitrobenzene (2-Nitro-1,4-phenylenediamine)

1-Amino-2-nitro-4-acetamidobenzene:

1,4-diamino-2-nitrobenzene (2-nitro-1,4-phenylenediamine) was selectively acetylated according to the method of McFarlane et. al, J. Chem. Soc. Perkin Trans., 691 (1988) incorporated herein by reference. The amine meta to the nitro group is readily acetylated using acetic anhydride in acetone (the amine ortho to the nitro group is strongly deactivated). The yield of 1-Amino-2-nitro-4-acetamidobenzene (2-nitro-4-acetamido aniline) was >90%. Characterization: $^1$H NMR (CD$_3$OD) δ [ppm]: 8.3 (m, 1 H, ArH), 7.5 (M, 1 H, ArH), 6.9 (M, 1 H, ArH), 2.1 (s, 3 H, acetyl CH3) in good agreement with McFarlane. IR (nujol/NaCl) ν [cm$^{-1}$]: 3470 (s, str, HOAc), 3340–3150 (m, m/str, acetamide ArNH+ArNH$_2$), 1661 (s, str, acetamide CO), 1643 (s, str, H bonded acetamide CO), 1592 (s, m/w, aryl stretch), 1547 (s, str, ArNO$_2$) & 1512 (s, m ArNO$_2$). Anal. (Dried at 80 ° C.) Calcd for C$_8$H$_9$N$_3$O$_3$: C, 49.23; H, 14.65; N, 21.53. Found: C, 49.36; H, 4.55; N, 21.31.

1,2-Diamino-4-acetamidobenzene:

1-Amino-2-nitro-4-acetamidobenzene was reduced to 1,2-Diamino-4-acetamidobenzene in acetic acid (HOAc)/MeOH using catalytic hydrogenation over a 10% Pd/C catalyst. The material was isolated as the dihydrochloride salt. Yield >90%. Characterization: $^1$H NMR (CD$_3$OD) δ [ppm]: 6.94 (m, 1 H, ArH), 6.68 (m, 1 H, ArH), 6.62 (m, 1 H, ArH), 2.1 (s, 3 H, acetyl CH$_3$). IR (nujol/NaCl) ν [cm$^{-1}$]: 3348 (s, str, acetamide ArNH), 3226–3100 (m, m, ArNH$_2$), 2588 (s, br, str, ArNH$_3^+$), 1649 (s, str, acetamide CO), 1623 (s, str, H bonded acetamide CO). Anal. (Dried at 80 ° C.) Calcd for C$_8$H$_{13}$N$_3$OCl$_2$ (HCl/H$_2$O)$_{0.1}$: C, 39.45; H, 5.50; N, 17.25; Cl, 30.57. Found: C, 39.39; H, 5.53; N, 17.32; Cl, 30.37. Presence of solvate HCl/H$_2$O was confirmed by IR, and is consistent with the constant boiling 36.5–38% HCl used to generate the hydrochloride salt.

C. 2,4-Diamino-2,4-Dimethyl Pentanone from 2,4-dimethylpentanone 2.4-Dibromo-2.4-dimethylpentanone:

To 2,4-dimethylpentanone (85 mL, 68.5 g, 0.60 mol) in CCl$_4$ or 1,2 Dichloroethane (1 L) was added N-bromosuccinimide (NBS, 240 g, 1.35 mol, 2.26 equiv). The mixture was heated under reflux, and benzoyl peroxide (ca 20 mg) was added to the refluxing mixture. While the solution was heated under reflux (24 h), a pale orange solid (succinimide) floated to the surface of the halogenated solvent, while unreacted NBS remained at the bottom. Benzoyl peroxide was repeatedly added to the refluxing mixture (ca 20 mg; 12–24 hr intervals) until no NBS was visible, usually the reaction was complete after 24 hours. When the reaction was complete, the solids were collected by filtration and discarded, the halogenated solvent/$Br_2$ was removed from the mother liquor under reduced pressure, leaving a pale yellow oil. To remove residual halogenated solvent, 95% EtOH (100 mL) was added, solvents were again removed under reduced pressure, and a yellow slightly impure oil resulted (159.99 g, 0.59 mol, 98%). $^1$H NMR ($CDCl_3$) 2.1 (s). IR (neat/NaCl) ν [$cm^{-1}$]: 3375 (s, w, impurity OH), 3014, 2978, 2933 (s, str, CH), 2858 (s, w, CH), 1701 (s, str, ketone CO).

2,4-Diazido-2,4-dimethylpentanone:

A solution of 2,4-Dibromo-2,4-dimethylpentanone prepared as above or purchased from Lancaster Synthesis (89.8 g, 0.33 mol) in EtOH (1.2 L, 95%) was added to a solution of $NaN_3$ (Caution!, 47.2 g, 0.726 mol, 2.2 equiv) in water (0.6 L). The solution was heated under reflux (16 h) to give a pale orange solution. The EtOH was removed under reduced pressure until the solution became cloudy. The cloudy aqueous solution was extracted, still warm, with pentane (500 mL) three times, and the combined extracts were dried over $Na_2SO_4$ and concentrated to 300 mL under reduced pressure. Glacial acetic acid (100 mL) was then added, and the remaining pentane was removed under reduced pressure. This workup was required to remove any excess $NaN_3$ since the product is exposed to Pd/C in the next step, and care should be taken to avoid the formation of heavy metal azides (due to the risk of explosion). The solvent was removed from a small sample under reduced pressure to give a neat oil (<20 mg) for spectroscopic characterization: $^1$H NMR ($CDCl_3$): 1.54 (s). IR (neat) ν [$cm^{-1}$]: 2115 ($RN_3$), 1720 (ketone CO). It should be noted, for safety, that the organic azides produced in this and related azide based syntheses are never isolated in concentrated forms or as solids in quantities greater than 20 mg.

2,4-Diamino-2,4-dimethylpentan-3-one:

Glacial acetic acid (50 mL) was added to the HOAc solution of the dialkyl azide formed in the previous step, and this solution was added to 10% Pd/C (2.7 g). The mixture was hydrogenated at 50 psi (1 week) in a Parr hydrogenator. Because the reaction evolves one $N_2$ molecule for every $H_2$ molecule absorbed, the bomb was evacuated and repressurized 10 times with $H_2$ to 50 psi. ($H_2$ from the high pressure reservoir is not efficiently consumed.) The charcoal was removed by filtration, and HOAc was removed under reduced pressure. After HBr was added (48%, 76 mL), the mixture was dissolved in EtOH. The volatiles were removed under reduced pressure to yield a tan solid, which was washed with a mixture (200 mL) of THF (50%), EtOH (45%), and conc. HBr (5%) or with a mixture of THF (95%) and conc. HBr (5%). The resulting white powdery product was the dihydrobromide salt of 2,4-Diamino-2,4-dimethylpentan-3-one (56.2 g, 48% from 2,4-Dibromo-2,4-dimethylpentanone). Additional product may be collected from washings that have been pooled from several different preparations. The product must be stored as the dihydrobromide or dihydrochloride salt to protect the amines from oxidative degradation. Characterization: $^1$H NMR ($CDCl_3$/DMSO-$d^6$) of 2,4-diamino-2,4-dimethyl-pentan-3-one. 2 HBr: 8.62 (6H, s, br, $NH_3$), 1.77 (12 H, s, Me). IR (free base, nujol mull) ν [$cm^{-1}$]: 3460–3160 ($RNH_2$), 1690 (ketone CO). Anal. (Dried at 80° C.) Calcd for $C_7H_{16}N_2O$. $(HBr)_2$: C, 27.47; H, 5.93; N, 9.15; Br, 52.22. Found: C, 27.43; H, 5.91; N, 9.11; Br, 52.46.

Syntheses of Macrocyclic Tetraamido-N Donors Ligands

Example 2

Macro Linker Intermediate (A-L-A) synthesis, from α-methyl alanine and dimethyl malonyl dichloride (a Tetramethyl Dimethyl substituted intermediate).

Hexamethyl (HM) Intermediate

Place a two-neck flask (1 L) fitted with a pressure equalizing addition funnel (250 mL) and a septum under $N_2$. Add α-amino isobutyric acid (i.e. α-methyl alanine) (20.62 g, 0.2 mol) and dry pyridine (250 mL, dryed over 4 Å mol sieves) to the flask and heat 55°–65° C. with stirring, then add dimethyl malonyl dichloride (17.8 mL, 0.135 mol) dissolved in dry pyridine (100 mL, dryed over 4 Å mol sieves) to the addition funnel. Add the contents of the addition funnel (dropwise, 1 h) to the reaction and the allow the acylation to proceed (60°–70° C., 30–36 h) under $N_2$ or with a drying tube fitted. Once the acylation is complete, quench the reaction by adding $H_2O$ (30 mL) and stirring (60°–70° C., 24 hrs). Reduce the solvent volume on the rotary evaporator to give an oil, then add HCl (conc., ca. 25 mL) to a final pH of 2–3. Set the hot solution in the refrigerator (4° C., 15 h), and the collect the resulting product by frit filtration, and wash thoroughly with acetonitrile (2×100 mL). The air-dried white product, (16.5–19.8 g, 45–60% yield) should be stored in a dessicator. This product is usually pure enough for ring closure reactions, but recrystallization may occasionally be required. Characterization: $^1$H NMR ($d^5$ pyridine, δ [ppm]); 9/2–9.8 br s, 2 H (carboxylic OH), 8.23 s, 2H (amide), 1.87 s 12 H ($CH_3$), 1.74 s 6 H ($CH_3$). IR (nujol/NaCl) ν [$cm^{-1}$]: 3317.0 (amide NH); 1717.9 (carboxylic CO); 1625.7 (amide CO). Anal. (dried at 100° C.) Calcd. for $C_{13}H_{22}N_2O_6$; C 51.63, H 7.34, N 9.27. Found; C 51.64, H 7.35, N 9.33.

Example 3

Large Scale, Macro Linker Intermediate (A-L-A) synthesis, from α-methyl alanine and diethyl malonyl dichloride (a TMDE substituted intermediate).

If a large scale synthesis is desired, a two-neck flask (2 L, RB+Claisen) should be fitted with a pressure equalizing addition funnel (250 mL) and septa, and placed under $N_2$. Add α-aminoisobutyric acid (i.e. α-methyl alanine) (90.3 g, 0.9 mol) (or any α- or β-amino described herein), cannulate anhydrous pyridine (1.4 L, sure seal) into the flask and heat the reaction mix to 45°–55° C. and stir. Cannulate Pyridine (100 mL, sure seal) and then dimethyl malonyl dichloride (104.4 mL, 0.61 mol) into the addition funnel. Add the contents of the addition funnel (dropwise, 3–4 h) to the reaction, remove the addition funnel, and allow the acylation to proceed (55°–65° C., 120–130 h) under $N_2$. Once the acylation is complete, quench the reaction by adding $H_2O$ (100 mL) and stirring (60°–70° C., 24–36 hrs). Reduce the solvent volume on the rotary evaporator to give an oil, then add HCl (conc., ca. 110 mL) to a final pH of 2–3. Set the hot solution in the refrigerator (4° C., 15 h), and collect the resulting product by frit filtration, and wash thoroughly with acetonitrile (700 mL, 150 mL) by stirring in an erlenmeyer flask. Crush the air-dried white product (87.9 g, 60% yield), in a mortar and pestle and store in a dessicator. The large scale reaction amide intermediate product is more likely to need recrystallization before use in ring closure reactions.

Example 4

Recrystalization of HM Intermediate

Crude intermediate from Example 2 or 3 (50.4 g, 0.153 mol) in $H_2O$ (slightly less than 500 mL, deionized) is dissolved by adding $Na_2CO_3$ (16.2 g, 0.153 mol) in three aliquots slowly and carefully to avoid excessive frothing. Stir good and heat mildly. Bring the solution to a boil, filter and acidify with HCl (conc., 30 mL, 0.36 mol). Allow the solution to cool (overnight, 4° C.) and filter the precipitate off and wash with acetonitrile (250 mL). The air dried product (38.8–45.4 g, recryst. yield 77–90%) should be stored in a dessicator.

Macrocyclization Reactions

Several synthetic routes for the preparation of macrocyclic tetraamido ligands have been developed. The organic azide based route is described in Uffelman, E. S., Ph.D. Thesis, California Institute of Technology (1992) and Kostka, K. L., Ph.D. Thesis Carnegie Mellon University (1993). Examples of several synthetic routes for the preparation of macrocyclic tetraamido ligands using a new synthetic method follow.

Phosphorus Trichloride Coupling

Phosphorus trichloride coupling of the amide intermediate reaction product to aromatic 1,2-diamines yields macrocyclic tetraamides safely, cheaply and in high yield. Two distinct variations of the $PCl_3$ coupling method are useful, the differences relate to the order of addition and choice of reagents utilized. These methods are applicable to the preparation of a wide variety of different macrocycles with different electronic substituents present on the bridge diamine, or steric substituents present on the amide intermediate, primarily because of the parallel incorporation of the macro, linker type of amide intermediates into all of the syntheses.

Example 5

A. Macrocycle Synthesis via $PCl_3$ Coupling

A long neck flask (250 mL) is charged with the amide intermediate of Examples 2–4, (10 mmol) and a stir bar and then baked in the oven (80°–100° C., 30–45 mins). The hot flask is placed under $N_2$, aryl diamine (10 mmol) is added and anhydrous pyridine (50 mL, sure seal) cannulated in. The flask is heated (50°–60° C.) and $PCl_3$ (d=1.574 g/mL, 1.72 mL, 20 mmol) syringed in as quickly as possible without excessive refluxing. This is an exothermic reaction, so caution should be used. The temperature is then increased to reflux or just below reflux (100°–115° C.) and the reaction allowed to proceed under $N_2$ (48 h). After the acylation is complete, the contents of the flask are acidified with HCl (1 eq., ca. 60 mL) to a final pH≈2. The mixture is transferred to an erlenmeyer (water is used to rinse the flask) and stirred with $CH_2Cl_2$ (300 mL, 2–3 h), then extracted with additional $CH_2Cl_2$ (2×150 mL). The combined organic layers are washed with dilute HCl (0.1M, 2×100 mL) followed by dilute aqueous $Na_2CO_3$ (2×5 g/100 mL). The organic solvents are removed on the rotary evaporator to yield crude product (30%). The weight of crude product is usually equivalent to the initial weight of diamine.

B. Macrocycle Synthesis via $PCl_3$ Coupling

A long neck flask (250 mL) is charged with $MgSO_4$ (5 g), a stir bar, aryl diamine (10 mmol) and pyridine (50 mL, dryed over 4 Å mol sieves) then placed under $N_2$. $PCl_3$ (d=1.754 g/mL, 1.72 mL, 20 mmol) is added via syringe and the mixture brought to reflux for 30 mins, an orange/yellow precipitate forms. The mixture is cooled somewhat, an amide intermediate (10 mmol) is added, then the mixture is refluxed under $N_2$ (115° C., 48 h). After the acylation is complete, the contents of the flask are acidified with HCl (1 eq., ca. 60 mL) to a final pH≈2. The mixture is transferred to an erlenmeyer and stirred with $CH_2Cl_2$ (300 mL, 2–3 h), then extracted with additional $CH_2Cl_2$ (2×150 mL). The combined organic layers are washed with dilute HCl (0.1M, 2×100 mL) followed by dilute $Na_2CO_3$ (2×5 g/100 mL). The organic solvents are removed on the rotary evaporator to yield crude product (30%). The weight of crude product is usually equivalent to the initial weight of diamine. Note: For larger scale macrocyclization reactions, the ring closure times are increased to 4–5 days at reflux, and most of the pyridine present at the end of the reaction is removed via rotary evaporation prior to acidification.

Example 6

HM-DCB from HM Intermediate+DCB Diamine 1,2-Diamino-4,5-Dichlorobenzene (1.77 g, 10 mmol) was utilized as the diamine with Hexa Methyl amide intermediate (3.02 g, 10mmol) in the $PCl_3$ method A or B macrocyclization reaction. The crude macrocycle (1.33 g, 30%) was recrystallized from a minimum of hot n-propanol by evaporation, 1st crop recrystallization yield was 60%. Characterization: $^1H$ NMR δ [ppm]: 7.69 (s, 2 H, ArH), 7.39 (s, 2 H, amide NH), 6.44 (s, 2 H, amide NH), 1.58 (s, 12 H, arm methyls), 1.53 (s, 6 H, malonate methyls), small n-propanol peaks were noted. IR (nujol/NaCl) ν [$cm^{-1}$]: 3503 (s, br, m-w, n-propanol OH, 3381 (sh, m, amide NH), 3338 (s, str, amide NH), 1689 (s, str, amide CO), 1643 (s, str, amide CO). Anal. Calcd. for $C_{19}H_{24}N_4O_4Cl_2 \cdot (C_3H_8O)_{0.2}$: C, 51.70; H, 5.57, N 12.30% Found C, 51.69; H, 5.63; N, 12.33%.

Oxazalone Coupling Reactions

Oxazalone coupling of the amide intermediate to aromatic diamines also yields macrocyclic tetraamides safely, cheaply and in high yield, but with less sensitivity to additional functional groups. The macrocycles able to be formed via the $PCl_3$ coupling route can also be manufactured via the oxazalone coupling route. In addition, the lesser sensitivity to additional functional groups has opened up the preparation of macrocyclic ligands with additional functional groups designed to confer new properties on the resulting metal complexes. Specific examples include the incorporation of reactive groups (such as amine or vinyl groups) attached in a pendant fashion to the aryl ring of the macrocycle allowing for covalent attachment of the preformed macrocycles to some (polymeric) substrate.

Example 7

Macrocycle Synthesis via Oxazalone Method

A long neck flask (250 mL) is charged with amide intermediate (3.3 g, 10 mmol), a stir bar and then baked in the oven (80°–100° C., 30–45 mins). The hot flask is fitted with a septum and placed under $N_2$. Anhydrous pyridine (50 mL, sure seal) is cannulated in and heating commenced while trimethyl acetyl chloride (i.e. pivaloyl chloride)

(22–24 mmol) is added via syringe. The temperature is increased to reflux or just below reflux (100°–115° C.) and the reaction allowed to proceed under $N_2$ (22–26 h) being careful to avoid cross contamination from other reactions on the $N_2$ line. The reaction goes from a clear pale yellow to a yellow-brown color. After oxazalone formation is complete§, the aryl diamine (8–10 mmol) is added either as a neat solid or via large bore cannula as a slurry in anhydrous pyridine, or dissolved and degassed under $N_2$ in anhydrous (sure seal) pyridine, if head space and solubility constraints can be satisfied. The ring closure reaction is refluxed for a further 48–72 hours (longer times for larger scales) under $N_2$ without cross contamination from other reactions. The mixture will usually turn brownish black. Once the acylation is complete, the reaction is quenched by adding $H_2O$ (30 mL) and stirring at reflux (100° C., 22–26 hrs). The mixture is cooled and transferred to an RB flask (500 mL) using a minimum of $H_2O$ to rinse the long neck flask. The solvent is removed via rotary evaporation to yield the crude product mixture as an oily tan to brownish black solid. It should be noted that, functional groups permitting, the crude product mixture can be taken up in $CH_2Cl_2$ and washed with dilute aqueous HCl and dilute aqueous $Na_2CO_3$. Removal of the organic solvent at reduced pressure then yields the normal macrocyclic product familiar from the $PCl_3$ coupling reactions and suitable for direct recrystallization as detailed previously to yield pure macrocyclic product.

§Pumping an aliquot down and redissolving in dry $d^5$ pyridine yielded a dominant species (>80% bis oxazalone after 24 h at reflux) with $^1H$ NMR δ [ppm]: 2.10 (q. 4 H, methylene $CH_2$'s), 1.38 (s, 12 H, $RCH_3$), 0.85 (t, 6 H, ethyl $CH_3$'s). Addition of water to the NMR sample regenerated the normal amide intermediate spectrum after about 20 h at RT.

Example 8

TMDE-AcB from TMDE Intermediate+AcB Diamine via oxazalones. This macrocycle is the protected form of an amino pendant macrocycle which can be attached to a range of different supports through amide formation between the substrate and the pendant amino group. Due to what is speculated to be formation of an unfavorable hydrogen bond, the ring closure reaction requires lengthy reflux times in order to achieve macrocyclization. 1,2-Diamino-4-acetamidobenzene dihydrochloride (9 mmol) was employed as the diamine in an oxazalone ring closure reaction. The macrocyclization time was increased (reflux, 5 days), followed by the normal quenching reaction and acid base workup to yield a mixture of a triamido containing macrocyclic imidazole and the desired tetraamido macrocycle. Further purification was by silica gel chromatography (1"×4–5") using acetonitrile as the eluant. Alternatively, the crude product can be purified by recrystallization from hot ethanol, chloroform or dichloroethane. Yield 15–20% from diamine. Characterization: $^1H$ NMR ($CD_3CN$) δ [ppm]: 8.31 (s, 1 H, aryl acetamide NH), 7.72 (m, 1 H, ArH), 7.55 (s, 1H, aryl amide NH), 7.44 (s, 1H, aryl amide NH), 7.30 (m, 2 H, ArH), 6.86 (s, 2 H, alkyl amide NH), 2.05 (q, 4 H, ethyl $CH_2$'s), 2.01 (s, 3 H, acetyl $CH_3$), 1.49 (d, 12 H, $RCH_3$'s), 0.82 (t, 6 H, ethyl $CH_3$'s). IR (nujol/NaCl) ν [cm$^{-1}$]: 3368 (s, m, amide NH), 3319 (s, m, amide NH), 3291 (sh, m, amide NH), 3268 (s, str, amide NH), 1678 (sh, m, amide CO), 1667 (s, str, amide CO), 1656 (s, str, amide CO), 1639 (sh, m, amide CO), 1608 (s, m, aryl ring/amide). Anal. Calcd for $C_{23}H_{33}N_5O_5 \cdot (H_2O)_{1.25}$: C, 57.31H, 7.42 N, 14.53 Found: C, 57.02; H, 7.15; N, 14.33. Presence of solvate $H_2O$ was confirmed by $^1H$ NMR and IR

Example 9

Synthesis of a peralkylated macrocycle (MAC*), or TMDM-DMP from the TMDM intermediate+2,4-Diamino-2,4-dimethyl-Pentan-3-one (DMP) via the Oxazalone Route.

The $PCl_3$ route to $H_4$[MAC*] (TMDM-DMP) fails to produce appreciable amounts of macrocycle due to what is speculated to be unfavorable complex formation between the diamine ketone functionality and the phosphorus reagent. Unlike the $PCl_3$ route, which is heterogeneous, the oxazalone route to $H_4$[MAC*] is a homogeneous solution method which simplifies the application of diagnostic techniques such as $^1H$ NMR to diagnose causes of synthetic failure. Reaction of TMDM bis oxazalone with DMP diamine in dry pyridine fails to form any amides (by NMR analysis). Since the oxazalone route is insensitive to ketone functionalities, the failure to form amides was attributed to acid salt formation of the alkyl amine functionality, the alkyl diamine is 3–4 p$K_a$ units more basic than pyridine while aryl diamines have p$K_a$'s close to that of pyridine. Therefore, a more basic high boiling solvent (triethylamine, tripropylamine, diethylaniline) may be used to increase the amount of amide formation. For amine containing solvents, the presence of water and impurity amines is problematic considering the low solubility of the reactants. Addition of a lewis acid drying agent was found to be beneficial. An appreciable yield of $H_4$[MAC*] can be obtained (2–3% macrocyclization yield, unoptimized) from the reaction (1 step) of TMDM bis oxazalone with DMP alkyl diamine in refluxing tripropylamine+CaO. Isolation of the product should be by fractional recrystallization from toluene in combination with $^1H$ NMR analysis.

The highest possible yield of $H_4$[MAC*] from alkyl diamine via the prior art method of Uffelman (4 steps from the alkyl diamine) is 8–10%. $H_4$[MAC*] can be obtained in appreciable yield via the oxazalone route.

Synthesis of Chelate Complexes

Figure 6:
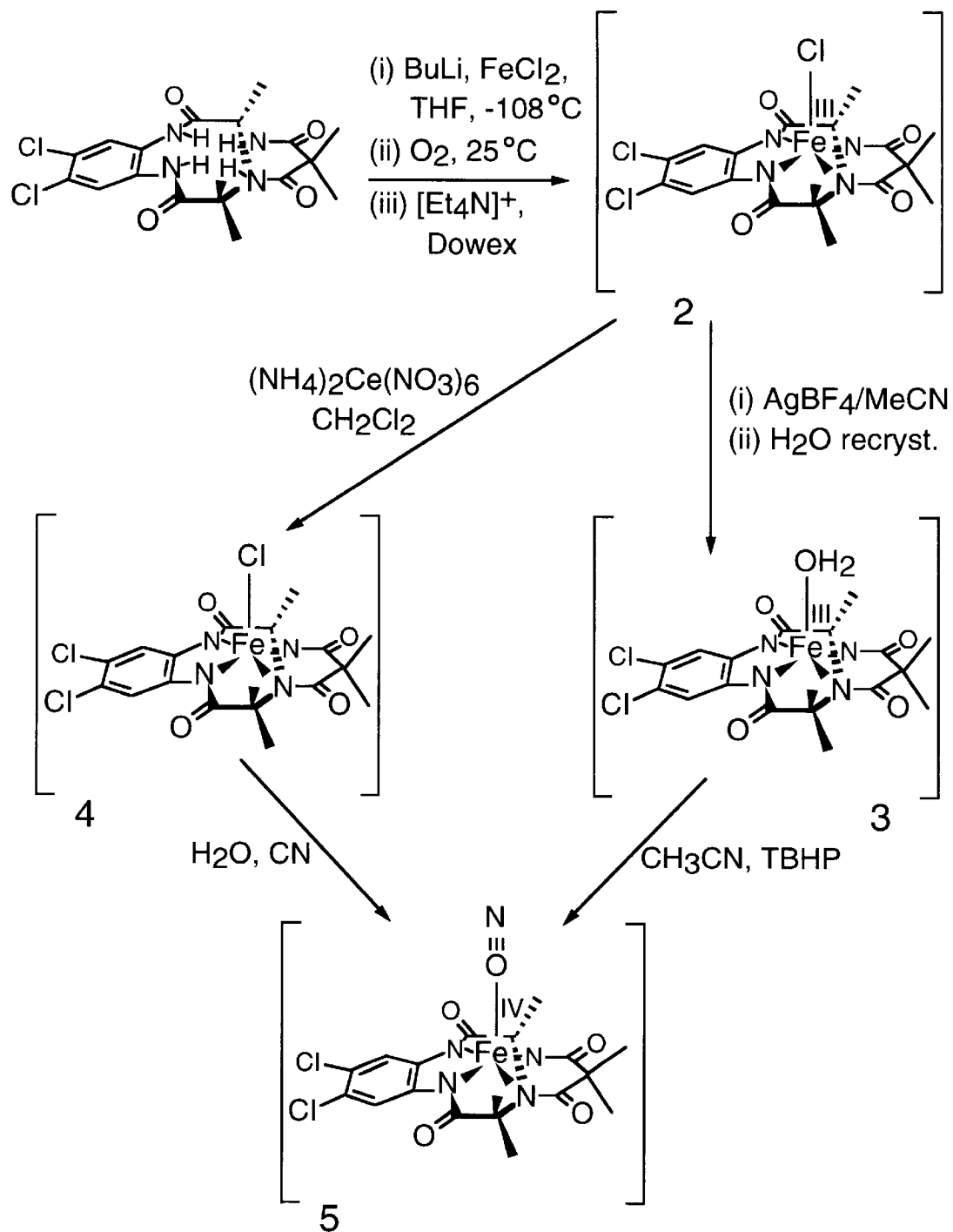
FIG. 6 is an illustration of several chelate complexes formed from the macrocyclic ligands of the invention.

The compounds labeled 2, 3, 4 and 5 in the following examples are the dimethyl counterparts of those illustrated in FIG. 6.

Example 10

[Et$_4$N]2 and [Et$_4$N]3. [the tetraethylammonium salts of iron(III) chloro TMDM-DCB monoanion and iron(III) aquo TMDM-DCB monoanion respectively].

The parent macrocyclic tetraamide of any of the foregoing examples (525 mg, 1.1 mmol) is dissolved in tetrahydrofuran (40 mL, Aldrich) under $N_2$. Tert-butyllithium under $N_2$ (2.6 mL, 4.4 mmol, 1.7M in 2,4-dimethylpentane, Aldrich) is added to the solution under N, at −108° C. Ferrous chloride (anhydrous, 155 mg, 1.2 mmol, Alfa) is added and the solution is warmed to room temperature with stirring (16 h), to yield a precipitate, an air sensitive Fe$^{II}$L complex. Air is admitted through a drying tube (2 h), and the solid is collected and washed with $CH_2Cl_2$ (2×10 mL). The resulting powder is dried under reduced pressure. Yield: 595 mg (≈93%). Because of variable solvation and limited solubility, the lithium salt should be converted to the tetraethylammonium salt for further use. The lithium salt (595 mg) in $CH_3OH$ (50 mL) is loaded on an ion exchange column (Dowex® 50X2-100, 25 g, 2 cm×12.5 cm) that is presaturated with [Et$_4$N]$^+$ cations, and the band is eluted with $CH_3OH$ (100 mL) The solvent is removed under reduced pressure. The residue is suspended in $CH_2Cl_2$ (20 mL) and the mixture filtered. The solvent is removed from the mother liquor under reduced pressure giving a hygroscopic glassy residue of [Et$_4$N]2 that may be used without further purification. IR (Nujol/NaCl, cm$^{-1}$): 1619 (ν(CO)amide), 1575 (ν(CO)amide), 1534 (ν(CO)amide). Careful purification of an iron(III) starting material is more conveniently approached by dealing with the axial aqua monoanionic complex rather than this axial chloro dianionic complex. [Et$_4$N]2 (550 mg, ca. 0.7 mmol) was dissolved in $CH_3CN$ (50 mL). Silver tetrafluoroborate (140 mg, 0.7 mmol) is dissolved in CH$_3$CN (2 mL) and added to the solution which is stirred (1 h). The AgCl precipitate is filtered off and the solvent removed under reduced pressure. The resulting [Et$_4$N]3 is further purified by elution through a silica gel column (8% MeOH in CH$_2$Cl$_2$). The solvent is removed under reduced pressure and the product is recrystallized from H$_2$O.

Example 11

[Et$_4$N]4. [the tetraethylammonium salt of iron (IV) chloro TMDM-DCB monoanion].

[Et$_4$N]2 (500 mg, ca. 0.6 mmol) was dissolved in CH$_2$Cl$_2$ (30 mL). Ammonium cerium(IV) nitrate (10.3 g, 18.3 mmol) is added to the solution and the mixture stirred (2 h). The solid cerium salts are removed by filtration. The product is obtained by removing the solvent under reduced pressure and drying under vacuum.

Example 12

Synthesis of [Ph$_4$P]5 [the tetraphenylphosphonium salt of iron(IV) cyano TMDM-DCB monoanion] from [Et$_4$N]4 [the tetraethylammonium salt of iron (IV) chloro TMDE-DCB monoanion] and NaCN.

[Et$_4$N]4 [the tetraethylammonium salt of iron(IV) chloro TMDM-DCB monoanion] (225 mg, 0.33 mmol) is suspended in H$_2$O (10 mL). Sodium cyanide (140 mg, 2.85 mmol) is dissolved in H$_2$O (10 mL) and added to the suspension and the mixture sonicated (Branson 1200, 0.5 h). The mixture is filtered and the blue product is precipitated by adding PPh$_4$Cl [tetraphenylphosphonium chloride] dissolved in water (600 mg, 1.6 mmol, 10 mL, Aldrich). The precipitate is collected and washed with H$_2$O (2×10 mL). The material should be extracted from the silica gel with CH$_3$CN:CH$_2$Cl$_2$ (1:1, 60 mL). The solvent is removed under reduced pressure and the residue dissolved in CH$_2$Cl$_2$ (3 mL) and filtered. Addition of pentane (150 mL) will give a powder (90 mg, 0.10 mmol)

Example 13

The Synthesis of [Ph$_4$P]5 [the tetraphenylphosphonium salt of iron(IV) cyano TMDM-DCB monoanion] from Nitrile Cyanide Sources.

[Ph$_4$P]5 [the tetraphenylphosphonium salt of iron(IV) cyano TMDM-DCB monoanion] can be formed in the presence or absence of base. In the absence of base, the color fades as the solvent is removed in the workup procedures. Therefore, product isolation to obtain the solid is best carried out in the presence of added base at a pH range of 9–10. The following reaction will yield 5 with each of CH$_3$CN, CD$_3$CN, CH$_3$CH$_2$CN and (CH$_3$)$_2$CHCN as the solvent substrates. Base is not added to the catalytic reactions described.

Example 14

The Synthesis of [Ph$_4$P]5 in the Presence of Base.

[Et$_4$N]3 (160 mg, 0.23 mmol) is dissolved in the chosen nitrile solvent (6 mL). See Example 13. Tetraethylammonium hydroxide base is added (20 wt %, 0.370 mL, 0.52 mmol, Aldrich), then t-butyl hydroperoxide (90%, 0.605 mL, 5.4 mmol, Aldrich) is added dropwise with stirring (20 min) resulting in a blue solution. The remaining nitrile is removed under reduced pressure, leaving an oily residue which is dissolved in H$_2$O (15 mL) and filtered. The material is precipitated from the filtrate by addition of an aqueous solution of PPh$_4$Cl (800 mg, 2.1 mmol, Aldrich, 10 mL). The blue precipitate is collected and washed with H$_2$O (2×10 mL). Yield: 130 mg, 0.15 mmol (65%). Further purification was carried out as described in the [Ph$_4$P]5 section, Example 12.

Example 15

1-[2-((E)-2-butenyl-2-ethylamido)-2-methylpropanamido]-2-[5,5-dimethylhydantoin]-4,5-dichlorobenzene (i.e. a ligand decomposition product).

[Et$_4$N]2 (130 mg, 0.13 mmol) is dissolved in CH$_3$CN (5 mL, Aldrich). A 90% solution of t-butyl hydroperoxide (0.445 mL, 4 mmol, Aldrich) is added slowly (3 min). The reaction mixture is stirred (25 min) and then all liquids removed under reduced pressure. The residue is dissolved in CH$_2$Cl$_2$ and loaded onto a preparative thin layer chromatography (TLC) plate (Silica gel GF, 1000 μm, 20 cm×20 cm) and eluted with a 15% CH$_3$CN/85% CH$_2$Cl$_2$ solvent mixture. The product band is detected under UV irradiation at an Rf value of 0.3. The portion of the silica that contains the product is removed from the preparative plate and the product should be extracted with CH$_2$Cl$_2$:CH$_3$CN (1:1). The solution is filtered and the solvent removed under reduced pressure. A solid is obtained by dissolving the residue in CH$_2$Cl$_2$ (3 mL) followed by addition of pentane (150 mL). This is collected by filtration and washed with pentane (2×10 mL).

Some examples of specific embodiments of the macrocyclic compounds of the present invention are disclosed in co-pending patent application of T. Collins et al., entitled "Metal Ligand Containing Bleaching Compositions" filed on even date herewith.

What we claim is:

1. A compound comprising:
a macrocyclic tetradentate ligand of the structure

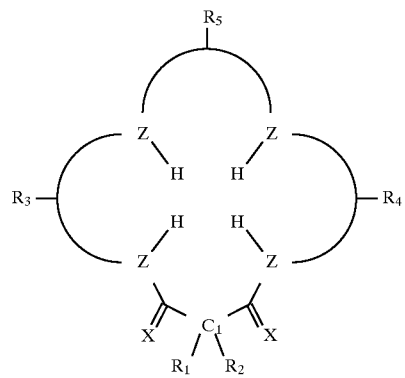

wherein R$_1$ and R$_2$ are the same or different, linked or nonlinked, and each is selected from the group consisting of substituents which are unreactive, form strong bonds intramolecularly within said R$_1$ and R$_2$ and with the cyclic carbon C$_1$, are sterically hindered and are conformationally hindered such that oxidative degradation of a metal complex of the compound is restricted when the complex is in the presence of an oxidizing medium;

Z is a metal complexing atom N;

X is O or NR, wherein R is alkyl, aryl, halogenated alkyl, halogenated aryl, methyl, hydroxy, oxylic, CF$_3$, CH$_2$CF$_3$;

wherein both Z and X are resistant to oxidative degradation such that each confers resistance to oxidative degradation to the metal complex of the compound when the complex is in the presence of an oxidizing medium;

$R_3$ is a unit joining the adjacent Z atoms comprised of

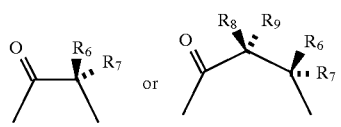

wherein $R_6$, $R_7$, $R_8$ and $R_9$ pairwise and cumulatively are the same or different and each is selected from the group consisting of alkyl, aryl, halogen halogenated alkyls, halogenated aryls, and $CF_3$; and $R_4$ is a unit joining the adjacent Z atoms comprised of

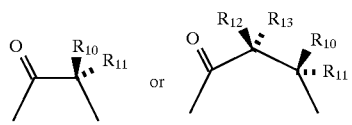

wherein $R_{10}$, $R_{11}$, $R_{12}$ and $R_{13}$ pairwise and cumulatively are the same or different and each is selected from the group consisting of alkyl, aryl, halogen halogenated alkyls, halogenated aryls and $CF_3$;

$R_5$ is a unit joining adjacent Z atoms selected from the group consisting of (i)

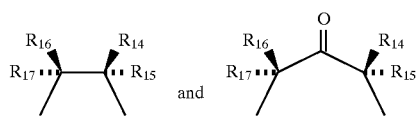

wherein $R_{14}$, $R_{15}$, $R_{16}$ and $R_{17}$ are the same or different and each is alkyl, aryl, halogen and $CF_3$, and (ii) mono-, di-, tri- and tetra-substituted aryl and heteroaryl substituents.

2. The compound recited in claim 1 wherein the aryl and heteroaryl substituents comprise

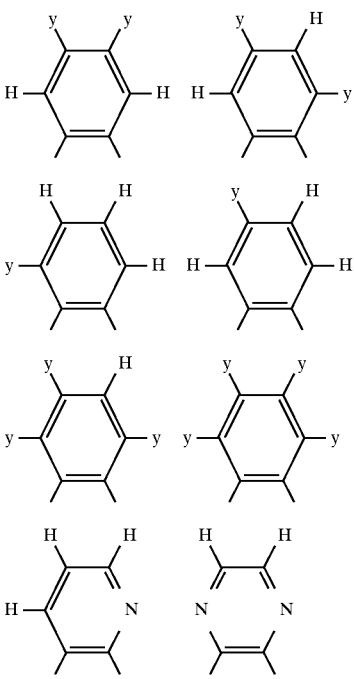

wherein each Y is the same or different and is selected from halogen, hydrogen, alkyl, aryl, amino, substituted amino, nitro, alkoxy and aryloxy.

3. The compound recited in claim 1 wherein each X is the same or different from the other X and each is selected from the group consisting of oxygen and $NR_s$.

4. The compound recited in claim 1 wherein each of $R_1$ and $R_2$ is selected from the group consisting of hydrogen, halogen, methyl, $CF_3$ or when taken cyclopentyl, cyclohexyl, cyclobutyl, cyclopropyl, substituted cyclopropyl, substituted cyclobytyl, substituted cyclopentyl or substituted cyclohexyl.

* * * * *